United States Patent
Joseph

(10) Patent No.: US 10,463,544 B2
(45) Date of Patent: *Nov. 5, 2019

(54) ORTHOPEDIC SYSTEM FOR IMMOBILIZING AND SUPPORTING BODY PARTS

(71) Applicant: EXOS LLC, Vista, CA (US)

(72) Inventor: Mark Joseph, Aspen, CO (US)

(73) Assignee: DJO, LLC, Vista, CA (US)

( * ) Notice: Subject to any disclaimer, the term of this patent is extended or adjusted under 35 U.S.C. 154(b) by 466 days.

This patent is subject to a terminal disclaimer.

(21) Appl. No.: 15/420,714

(22) Filed: Jan. 31, 2017

(65) Prior Publication Data

US 2017/0189241 A1  Jul. 6, 2017

Related U.S. Application Data

(63) Continuation of application No. 13/661,911, filed on Oct. 26, 2012, now Pat. No. 9,561,128, which is a continuation of application No. 12/013,449, filed on Jan. 13, 2008, now Pat. No. 8,303,527.

(60) Provisional application No. 60/945,277, filed on Jun. 20, 2007.

(51) Int. Cl.
*A61F 5/01* (2006.01)
*A61F 13/04* (2006.01)
*A61F 5/055* (2006.01)

(52) U.S. Cl.
CPC .............. *A61F 13/046* (2013.01); *A61F 5/01* (2013.01); *A61F 5/0102* (2013.01); *A61F 5/0111* (2013.01); *A61F 5/0118* (2013.01); *A61F 5/055* (2013.01); *A61F 13/04* (2013.01)

(58) Field of Classification Search
CPC ..................................................... A61F 5/0102

USPC .......... 602/8, 6, 5, 1; 2/455, 456, 462, 463; 128/869; 264/632, 653, 241, 654, 271.1, 264/259

See application file for complete search history.

(56) References Cited

U.S. PATENT DOCUMENTS

| 57,283 | A | 8/1866 | Brown |
| 2,019,360 | A | 10/1889 | Sanders |
| 482,647 | A | 9/1892 | Obear |
| D35,545 | S | 12/1901 | Schaefer |

(Continued)

FOREIGN PATENT DOCUMENTS

| CN | 2902232 | 5/2007 |
| CN | 101279110 | 10/2008 |

(Continued)

OTHER PUBLICATIONS

Johnson & Johnson Orthoplast Splinting Materials, http://www.medco-school.com/Supply/Product.asp?Leaf_ld-80365, archived 2007.
Aquaplast Splinting Materials, http://www.wisdomking.com/aquaplast-splinting, archived 2008.

(Continued)

*Primary Examiner* — Tarla R Patel
(74) *Attorney, Agent, or Firm* — Knobbe, Martens, Olson & Bear, LLP

(57) ABSTRACT

A unitized cast system for immobilizing and supporting a body part. The unitized casting system includes a first inner layer for padding and dissipating heat against the patient's skin. A second layer is formed from a thermoformable structural material such as perforated plastic. A protective third outer layer is provided to provide insulation for the second layer. These three layers are formed together to form a unitized cast system that is easily formed and applied to the patient.

20 Claims, 15 Drawing Sheets

(56) References Cited

U.S. PATENT DOCUMENTS

| | | |
|---|---|---|
| 911,243 A | 2/1909 | Johannesen |
| 975,734 A | 11/1910 | Tebeau |
| 1,082,542 A | 12/1913 | Manson |
| 1,360,840 A | 11/1920 | White |
| 1,477,070 A | 3/1922 | Martin |
| 1,471,948 A | 10/1923 | Cox et al. |
| 1,583,606 A | 5/1926 | Roussel |
| 2,070,810 A | 2/1937 | Saling |
| 2,181,689 A | 11/1939 | Bell |
| 2,206,404 A | 7/1940 | Jones |
| 2,477,040 A | 3/1945 | Brown et al. |
| 2,554,337 A | 5/1951 | Lampert |
| 2,736,314 A | 2/1956 | Hale |
| 2,759,475 A | 8/1956 | Swaay |
| 2,818,063 A | 12/1957 | Smith et al. |
| 2,904,040 A | 9/1959 | Hale |
| D198,069 S | 4/1964 | Connelly |
| D203,018 S | 11/1965 | Helferich |
| 3,230,952 A | 1/1966 | Reyes Terron |
| 3,302,642 A | 2/1967 | Allen |
| 3,306,284 A | 2/1967 | McKinley |
| 3,313,297 A | 4/1967 | Applegate et al. |
| 3,320,950 A | 5/1967 | McElvenny |
| 3,420,231 A | 1/1969 | Edenbaum |
| 3,490,444 A | 1/1970 | Larson |
| 3,512,523 A | 5/1970 | Barnett |
| 3,692,023 A | 9/1972 | Phillips et al. |
| 3,788,307 A | 1/1974 | Kistner |
| 3,896,843 A | 7/1975 | Millar et al. |
| 3,906,943 A | 9/1975 | Arluck |
| 3,916,885 A | 11/1975 | Gaylord, Jr. |
| 3,924,272 A | 12/1975 | Allen et al. |
| 4,006,741 A | 2/1977 | Arluck |
| 4,019,505 A | 4/1977 | Wartman |
| 4,136,686 A | 1/1979 | Arluck |
| 4,169,469 A | 10/1979 | Arluck |
| 4,193,395 A | 3/1980 | Gruber |
| D256,055 S | 7/1980 | Finnieston |
| 4,235,228 A | 11/1980 | Gaylord et al. |
| 4,240,415 A | 12/1980 | Wartman |
| D259,955 S | 7/1981 | Helferich |
| 4,286,586 A | 9/1981 | Potts |
| 4,316,457 A | 2/1982 | Liegeois |
| D266,288 S | 9/1982 | Coon |
| 4,379,463 A | 4/1983 | Meier et al. |
| D270,284 S | 8/1983 | Lindh et al. |
| 4,427,002 A | 1/1984 | Baron et al. |
| 4,441,711 A | 4/1984 | Dubar et al. |
| 4,442,834 A | 4/1984 | Tucker et al. |
| 4,454,873 A | 6/1984 | Laufenberg et al. |
| 4,471,993 A | 9/1984 | Watson |
| 4,473,671 A | 9/1984 | Green |
| 4,483,333 A | 11/1984 | Wellman |
| 4,510,927 A | 4/1985 | Peters |
| 4,531,241 A | 7/1985 | Berger |
| 4,572,167 A | 2/1986 | Brunswick |
| 4,584,993 A | 4/1986 | Nelson |
| 4,600,618 A | 7/1986 | Raychok, Jr. et al. |
| D287,640 S | 1/1987 | Primiano |
| 4,661,535 A | 4/1987 | Borroff |
| 4,726,361 A | 2/1988 | Farley |
| 4,765,319 A | 8/1988 | Finnieston et al. |
| 4,770,299 A | 9/1988 | Parker |
| 4,784,123 A | 11/1988 | Robeson |
| 4,827,915 A | 5/1989 | Gorsen |
| 4,872,448 A | 10/1989 | Johnson |
| 4,888,225 A | 12/1989 | Sandvig et al. |
| 4,912,174 A | 3/1990 | Grouiller |
| 4,946,726 A | 8/1990 | Sandvig et al. |
| 4,955,368 A | 9/1990 | Heimann |
| 5,031,607 A | 7/1991 | Peters |
| 5,038,759 A | 8/1991 | Morgenstern |
| 5,058,576 A | 10/1991 | Grim et al. |
| D326,719 S | 6/1992 | Eghamn |
| 5,158,098 A | 10/1992 | Jalalian |
| 5,180,361 A | 1/1993 | Moore et al. |
| 5,230,698 A | 7/1993 | Garth |
| 5,316,604 A | 5/1994 | Fell |
| RE34,714 E | 8/1994 | Burns et al. |
| 5,364,693 A | 11/1994 | Moren et al. |
| 5,366,439 A | 11/1994 | Peters |
| D357,745 S | 4/1995 | Radwell |
| 5,409,761 A | 4/1995 | Langley |
| 5,415,622 A | 5/1995 | Kelley |
| D363,780 S | 10/1995 | Darby et al. |
| 5,454,780 A | 10/1995 | Duback et al. |
| 5,520,529 A | 5/1996 | Heckel |
| D373,639 S | 9/1996 | McKie |
| 5,554,104 A | 9/1996 | Grim |
| 5,599,288 A | 2/1997 | Shirley et al. |
| 5,624,386 A | 4/1997 | Tailor et al. |
| 5,632,722 A | 5/1997 | Tweardy et al. |
| 5,688,229 A | 11/1997 | Bauer |
| 5,737,774 A | 4/1998 | Petty-Saphon et al. |
| 5,752,873 A | 5/1998 | Morris |
| 5,752,926 A | 5/1998 | Larson et al. |
| D395,514 S | 6/1998 | Stano |
| 5,763,047 A | 6/1998 | Green |
| 5,769,804 A | 6/1998 | Harris et al. |
| 5,807,291 A | 9/1998 | Larson et al. |
| 5,819,312 A | 10/1998 | Snyder et al. |
| 5,823,984 A | 10/1998 | Silverberg |
| 5,826,304 A | 10/1998 | Carlson |
| 5,830,167 A | 11/1998 | Jung |
| D405,180 S | 2/1999 | Reina |
| 5,865,778 A | 2/1999 | Johnson |
| 5,882,322 A | 3/1999 | Kim et al. |
| 5,902,259 A | 5/1999 | Wilkerson |
| 5,926,843 A | 7/1999 | Winchester |
| 5,934,599 A | 8/1999 | Hammerslag |
| 5,951,504 A | 9/1999 | Iglesias et al. |
| 5,971,946 A | 10/1999 | Quinn et al. |
| 5,982,285 A | 11/1999 | Bueche et al. |
| 6,042,557 A | 3/2000 | Ferguson et al. |
| 6,053,884 A | 4/2000 | Peters |
| 6,056,671 A | 5/2000 | Marmer |
| 6,056,713 A | 5/2000 | Hayashi |
| RE36,745 E | 6/2000 | Rudy, Jr. et al. |
| 6,093,161 A | 7/2000 | Vlaeyen et al. |
| 6,110,134 A | 8/2000 | Clark, Jr. et al. |
| 6,146,240 A | 11/2000 | Morris |
| D436,177 S | 1/2001 | Miller |
| 6,168,966 B1 | 1/2001 | Grim et al. |
| 6,179,798 B1 | 1/2001 | Nelson |
| D437,416 S | 2/2001 | Slautterback |
| 6,186,966 B1 | 2/2001 | Grim et al. |
| 6,202,953 B1 | 3/2001 | Hammerslag |
| 6,254,560 B1 | 7/2001 | Tweardy et al. |
| 6,289,558 B1 | 9/2001 | Hammerslag |
| 6,322,529 B1 | 11/2001 | Chung |
| 6,325,772 B1 | 12/2001 | Scheuermann et al. |
| 6,358,220 B1 | 3/2002 | Langen et al. |
| 6,416,074 B1 | 7/2002 | Maravets et al. |
| 6,423,020 B1 | 7/2002 | Koledin |
| D463,565 S | 9/2002 | Slautterback |
| 6,509,078 B1 | 1/2003 | Beckmann |
| 6,520,925 B1 | 2/2003 | Thibodo, Jr. |
| D473,653 S | 4/2003 | Weaver, II et al. |
| D477,088 S | 7/2003 | Brown et al. |
| D477,409 S | 7/2003 | Mills et al. |
| D477,410 S | 7/2003 | Wiggins et al. |
| 6,602,215 B1 | 8/2003 | Richie, Jr. |
| 6,663,581 B1 | 12/2003 | Calabrese |
| D492,787 S | 7/2004 | Weaver, II et al. |
| 6,779,282 B2 | 8/2004 | Grohninger |
| D496,465 S | 9/2004 | Weaver, II |
| D500,855 S | 1/2005 | Pick et al. |
| 6,843,190 B1 | 1/2005 | LaPierre-McAfee |
| 6,872,188 B2 | 3/2005 | Caille et al. |
| D505,727 S | 5/2005 | Krahner et al. |
| 6,893,410 B1 | 5/2005 | Hely |
| 6,922,917 B2 | 8/2005 | Kerns et al. |
| 6,960,176 B1 | 11/2005 | Hely et al. |
| 7,001,348 B2 | 2/2006 | Garth et al. |

(56) References Cited

U.S. PATENT DOCUMENTS

| | | |
|---|---|---|
| D518,895 S | 4/2006 | Weaver, II et al. |
| D519,211 S | 4/2006 | Doty et al. |
| 7,025,737 B2 | 4/2006 | Modglin |
| 7,041,073 B1 | 5/2006 | Patron |
| 7,056,298 B1 | 6/2006 | Weber |
| 7,082,701 B2 | 8/2006 | Dalgaard et al. |
| 7,083,585 B2 | 8/2006 | Latham |
| 7,090,653 B2 | 8/2006 | Moeller |
| D530,016 S | 10/2006 | Sroufe et al. |
| 7,141,031 B2 | 11/2006 | Garth et al. |
| 7,182,741 B2 | 2/2007 | Porrata et al. |
| 7,204,817 B1 | 4/2007 | Toronto et al. |
| D542,919 S | 5/2007 | Leatt |
| 7,217,060 B2 | 5/2007 | Ingimarsson |
| D550,370 S | 9/2007 | Peters et al. |
| D552,743 S | 10/2007 | Verkade et al. |
| D552,744 S | 10/2007 | Verkade et al. |
| D558,883 S | 1/2008 | Ortiz |
| 7,316,660 B1 | 1/2008 | Modglin |
| 7,329,229 B2 | 2/2008 | Scheinberg et al. |
| D565,189 S | 3/2008 | Gramza et al. |
| 7,392,602 B2 | 7/2008 | Reagan et al. |
| 7,399,288 B2 | 7/2008 | Chao |
| D580,064 S | 11/2008 | Lin et al. |
| D580,555 S | 11/2008 | Lin et al. |
| 7,449,006 B2 | 11/2008 | Wolanske |
| 7,470,243 B2 | 12/2008 | Garth |
| D584,822 S | 1/2009 | Weber |
| 7,507,215 B2 | 3/2009 | Ryan |
| 7,591,050 B2 | 9/2009 | Hammerslag |
| 7,597,671 B2 | 10/2009 | Baumgartner et al. |
| 7,608,052 B1 | 10/2009 | Baker |
| 7,645,250 B2 | 1/2010 | Koby et al. |
| 7,674,234 B2 | 3/2010 | Calco et al. |
| D616,556 S | 5/2010 | Hu |
| D617,464 S | 6/2010 | Weaver, II et al. |
| 7,727,172 B2 | 6/2010 | Wang |
| D626,242 S | 10/2010 | Sagnip et al. |
| D626,244 S | 10/2010 | Sagnip et al. |
| D628,300 S | 11/2010 | Caden |
| D628,696 S | 12/2010 | Robertson |
| D629,115 S | 12/2010 | Robertson |
| 7,846,118 B2 | 12/2010 | Sandhu |
| 7,854,714 B1 | 12/2010 | Weber et al. |
| 7,874,997 B2 | 1/2011 | Jaccard |
| D632,401 S | 2/2011 | Stevens |
| 7,883,485 B2 | 2/2011 | Moenning et al. |
| D633,622 S | 3/2011 | Chiang |
| D633,623 S | 3/2011 | Leatt et al. |
| D635,269 S | 3/2011 | Franke et al. |
| D635,270 S | 3/2011 | Chiang |
| D635,682 S | 4/2011 | Chiang |
| D636,494 S | 4/2011 | Garth et al. |
| D638,948 S | 5/2011 | Janzon |
| 7,942,837 B2 | 5/2011 | Clark et al. |
| 7,950,112 B2 | 5/2011 | Hammerslag et al. |
| D639,965 S | 6/2011 | Wehsely-Swiczinsky |
| 7,954,204 B2 | 6/2011 | Hammerslag et al. |
| 7,955,287 B2 | 6/2011 | Frangi |
| D641,482 S | 7/2011 | Robertson et al. |
| D641,483 S | 7/2011 | Robertson et al. |
| D643,978 S | 8/2011 | Abajo Alonso et al. |
| 7,992,261 B2 | 8/2011 | Hammerslag et al. |
| D647,623 S | 10/2011 | Thorgilsdottir et al. |
| D647,624 S | 10/2011 | Thorgilsdottir et al. |
| D649,648 S | 11/2011 | Cavalieri et al. |
| D649,649 S | 11/2011 | Leatt et al. |
| D649,650 S | 11/2011 | Wehsely-Swiczinsky |
| 8,057,417 B2 | 11/2011 | Imai |
| D650,485 S | 12/2011 | Jaccard |
| D652,937 S | 1/2012 | Robertson et al. |
| 8,091,182 B2 | 1/2012 | Hammerslag et al. |
| D654,180 S | 2/2012 | Weaver, II |
| D657,062 S | 4/2012 | Chiang |
| D657,063 S | 4/2012 | Chiang |
| D663,850 S | 7/2012 | Joseph |
| D663,851 S | 7/2012 | Joseph |
| D663,852 S | 7/2012 | Joseph |
| D664,259 S | 7/2012 | Joseph |
| D665,088 S | 8/2012 | Joseph |
| D666,301 S | 8/2012 | Joseph |
| D666,302 S | 8/2012 | Joseph |
| 8,246,560 B2 | 8/2012 | Gaylord et al. |
| 8,277,401 B2 | 10/2012 | Hammerslag et al. |
| 8,303,527 B2 | 11/2012 | Joseph |
| D687,566 S | 8/2013 | Joseph |
| 8,856,972 B2 | 10/2014 | Kirshon |
| 8,951,217 B2 | 2/2015 | Joseph |
| 9,295,748 B2 | 3/2016 | Joseph |
| 9,408,738 B2 | 8/2016 | Boraas et al. |
| 9,561,128 B2 | 2/2017 | Joseph |
| 2002/0068890 A1 | 6/2002 | Schwenn et al. |
| 2002/0095750 A1 | 7/2002 | Hammerslag |
| 2002/0148461 A1 | 10/2002 | Heinz et al. |
| 2002/0161114 A1 | 10/2002 | Gunatillake et al. |
| 2003/0178404 A1 | 9/2003 | Dimartino et al. |
| 2003/0204938 A1 | 11/2003 | Hammerslag |
| 2004/0024337 A1 | 2/2004 | Tseng et al. |
| 2004/0034316 A1 | 2/2004 | Castro |
| 2005/0033207 A1 | 2/2005 | Anders |
| 2005/0034686 A1 | 2/2005 | Spatt |
| 2005/0043664 A1 | 2/2005 | Reaux |
| 2005/0101898 A1 | 5/2005 | Cohen |
| 2005/0197606 A1 | 9/2005 | Preire |
| 2005/0251074 A1 | 11/2005 | Latham |
| 2005/0273030 A1 | 12/2005 | Koby et al. |
| 2005/0281999 A1 | 12/2005 | Hofmann et al. |
| 2006/0051402 A1 | 3/2006 | Bogardus et al. |
| 2006/0052730 A1 | 3/2006 | Hargrave et al. |
| 2006/0062991 A1 | 3/2006 | Sendijarevic et al. |
| 2006/0129075 A1 | 6/2006 | Scheinberg et al. |
| 2006/0155226 A1 | 7/2006 | Grim et al. |
| 2006/0156517 A1 | 7/2006 | Hammerslag et al. |
| 2006/0173390 A1 | 8/2006 | Van Wyk et al. |
| 2007/0004993 A1 | 1/2007 | Coppens et al. |
| 2007/0077393 A1 | 4/2007 | Chiang et al. |
| 2007/0179417 A1 | 8/2007 | Schwenn et al. |
| 2008/0060167 A1 | 3/2008 | Hammerslag et al. |
| 2008/0060168 A1 | 3/2008 | Hammerslag et al. |
| 2008/0066272 A1 | 3/2008 | Hammerslag et al. |
| 2008/0066345 A1 | 3/2008 | Hammerslag et al. |
| 2008/0066346 A1 | 3/2008 | Hammerslag et al. |
| 2008/0082033 A1 | 4/2008 | Ortiz |
| 2008/0083135 A1 | 4/2008 | Hammerslag et al. |
| 2008/0177210 A1 | 7/2008 | McDevitt Larson |
| 2008/0262400 A1 | 10/2008 | Clark et al. |
| 2009/0082707 A1 | 3/2009 | Rumsey |
| 2009/0192425 A1 | 7/2009 | Garth et al. |
| 2009/0192427 A1 | 7/2009 | Brown et al. |
| 2009/0204042 A1 | 8/2009 | Park |
| 2009/0204047 A1 | 8/2009 | MacArthur |
| 2009/0264802 A1 | 10/2009 | Chen |
| 2010/0168630 A1 | 7/2010 | Cropper et al. |
| 2010/0185130 A1 | 7/2010 | Rizo Patron |
| 2010/0262054 A1 | 10/2010 | Summit et al. |
| 2010/0268139 A1 | 10/2010 | Garth |
| 2010/0268140 A1 | 10/2010 | Berlese |
| 2010/0268141 A1 | 10/2010 | Bannister |
| 2010/0299959 A1 | 12/2010 | Hammerslag et al. |
| 2010/0318010 A1 | 12/2010 | Sandifer et al. |
| 2011/0034844 A1 | 2/2011 | Thorgilsdottir et al. |
| 2011/0082402 A1 | 4/2011 | Oddou et al. |
| 2011/0130694 A1 | 6/2011 | Livolsi et al. |
| 2011/0213284 A1 | 9/2011 | Garth et al. |
| 2011/0313389 A1 | 12/2011 | Wood et al. |
| 2012/0065562 A1 | 3/2012 | Kaphingst |
| 2014/0135672 A1 | 5/2014 | Joseph et al. |
| 2015/0119775 A1 | 4/2015 | Gildersleeve et al. |
| 2015/0238343 A1 | 8/2015 | Joseph |

(56) References Cited

U.S. PATENT DOCUMENTS

2016/0317342 A1   11/2016   Joseph
2017/0014216 A1    1/2017   Boraas et al.

FOREIGN PATENT DOCUMENTS

| EP | 0 393 003 | 10/1990 |
|---|---|---|
| EP | 0 401 883 | 12/1990 |
| EP | 0 619 102 | 10/1994 |
| EP | 0 625 342 | 11/1994 |
| EP | 0 795 307 | 4/2004 |
| JP | 09-234241 | 9/1997 |
| JP | 2004-065912 | 3/2004 |
| WO | WO 93/21967 | 11/1993 |
| WO | WO 07/035875 | 3/2007 |
| WO | WO 10/099130 | 9/2010 |
| WO | WO 11/071264 | 6/2011 |
| WO | WO 12/138523 | 10/2012 |

OTHER PUBLICATIONS

U.S. Appl. No. 12/181,272, filed Feb. 28, 2008. Inventor: Joseph.
International Search Report dated Oct. 10, 2008 in PCT Patent Application No. PCT/US2008/067570.
Written Opinion dated Oct. 10, 2008 in PCT Patent Application No. PCT/US2008/067570.
U.S. Appl. No. 12/436,089, filed May 5, 2009. Inventor: Joseph.
U.S. Appl, No, 12/710,252, filed Feb. 22, 2010. Inventor: Joseph.
U.S. Appl. No. 12/711,188, filed Feb. 23, 2010. Inventor: Joseph.
International Search Report dated Jul. 26, 2010, in PCT Patent Application No. PCT/US2010/25119.
Written Opinion dated Jul. 26, 2010, in PCT Patent Application No. PCT/US2010/25119.

ORTHOPEDIC SYSTEM FOR IMMOBILIZING AND SUPPORTING BODY PARTS

RELATED APPLICATIONS

This application is a continuation of U.S. application Ser. No. 13/661,911, filed Oct. 26, 2012, now U.S. Pat. No. 9,561,128, which is a continuation of U.S. application Ser. No. 12/013,449, entitled "Orthopedic System For Immobilizing And Supporting Body Parts," filed Jan. 13, 2008, now U.S. Pat. No. 8,303,527, which claims the benefit of U.S. Provisional Application No. 60/945,277, entitled "Orthopedic System For Immobilizing And Supporting Body Parts," filed Jun. 20, 2007, the disclosures of which are hereby incorporated by reference in their entireties.

FIELD OF THE INVENTION

This invention relates to the field of orthopedic systems for immobilizing and supporting human and or animal body parts and in particular, casts.

BACKGROUND OF THE INVENTION

The management of fractures and injuries to the extremities has a long and colorful history in medicine. Prior to the invention of plaster of Paris by the Flemish army surgeon Mathijsen in 1852, the stabilization of broken bones and sundry joint injuries was a haphazard affair using pieces of wood, branches, and any rigid material that might be available. Plaster of Paris was rubbed into muslin or linen cloth prior to its use, "a tedious process", and wrapped around an injured limb to provide stability. When the anhydrous calcium sulfate was recombined with water, the reaction produced the slow drying, but stiff gypsum. Manufactured rolls of plaster of Paris cast material were not available until the mid-1900's. The casts made in this way were messy to apply, often extremely bulky, could be very difficult to remove, would break down with walking, fell apart in water, were heavy, and made visualization of a fracture difficult with x-ray. Yet at the time they were a major step forward in the medical management of these unstable musculoskeletal injuries.

Plaster casts were used consistently and devotedly until the 1980's when fiberglass materials became available. Though more expensive and somewhat more difficult to work with, fiberglass soon became the preferred casting material in many clinics and hospitals and remains so today. It offered increased lightness, somewhat better visibility under x-ray, and was resistant to softening if wet. Unlike plaster rolls or strips which could remain open on the shelf, fiberglass would gradually harden if exposed to air and needed to be packaged in airtight bags. Fiberglass still required water activation to harden into a usable cast, and was highly user dependent in the quality of the final product. It has sharp edges, folded corners can produce skin ulcers, and it can be more difficult to remove than plaster. It is available in rolls of various sizes (2", 3", 4", 5", & 6") A cast saw with a good blade is necessary for its removal. Fiberglass and plaster remain the most commonly used material casting in orthopedics today.

A variation on fiberglass is the Delta-cast brand (distributed by BSN Medical) of roll fiberglass casting tape material that is more pliable and less rigid than fiberglass, has improved radiolucency and can be cut with a scissors as well as with a cast saw. It comes in rolls similar to fiberglass and is wrapped around the injured extremity over a cotton or fabric padding under-layer in the same fashion as plaster and fiberglass. It too is water activated. It is slightly more expensive than fiberglass, but has advantages of comfort and enough flexibility to be removed in some instances.

For the purposes of this discussion it is important to define splints, casts, and braces. While these are all used to support body parts, they are separate and distinct products, each constructed differently and for disparate uses.

Splints are typically rigid supports made of various substances, plaster, fiberglass, plastic, metal or inflatable materials, which temporarily support an injured extremity. They often are applied to only one surface of a limb and may be held in place by an elastic bandage, hook and loop, or other wrapping. They generally do not rigidly encircle a limb to allow for swelling in the early stages of an injury. Typically they are applied in an emergency setting, worn for less than a week, are discarded after transition to a more long term support system when seen in an orthopedic clinic. One common material used for splints is Ortho-Glass distributed by BSN Medical. This material is a limp fiberglass material impregnated with water activated resin and covered with a non-woven fabric. It is wetted and held to the body with elastic bandage while it cures in a few minutes.

Braces are usually employed as a removable, sometimes hinged, device to provide stabilization to a joint in which bones or ligaments may have been injured or for several weeks after removal of a cast to provide additional support during recovery of range of motion (ROM) and strength. Cast braces are an addition hybrid support system (Air Cast Walking Boot, CAM walkers, Sarmiento elbow brace) which typically utilize a rigid shell or strut system with a padded liner and may be removable depending on the nature of the injury (elbow dislocations, some stable ankle fractures, etc.) Materials such as Orthoplast distributed by BSN Medical and similar low temperature thermoformable plastic sheets are sometimes used for braces. These single layer plastic sheets material are heated in hot water to become formable and usually custom cut and formed in situ (in place on the body). Wrap closures are then added such as hook and loop, tape or bandages are used to secure them to the body.

Casts are typically a circumferential protective shell of plaster, synthetic composites, or fiberglass that will maintain the alignment of an injury. They may be worn for upwards of 3-12 weeks depending on the characteristics of the injury involved and the healing qualities of the patient. Currently, the vast majority of casts are assembled "in situ" (on the body) in a process where rolls of material, both padding and a wetted plaster or fiberglass resin layer, are successively wrapped circumferentially around the body part in multiple layers. Once completed, they completely encircle the body part in a continuous fashion that becomes rigid to some degree once the catalyst sets and typically can not be opened or adjusted without cutting through the layers of material.

The prior casting systems are designed to be constructed from multiple separate materials. This requires the practitioner to be skilled in utilizing these materials and applying these materials, such as plaster, fiberglass or Delta-cast to create the cast on the patient. Also, the padding must be applied initially before the casting material is applied. Any problems with either of the materials require the entire process to be restarted.

Another disadvantage of these systems is that they require multiple layers of material to complete the process and are time consuming to apply. Padding is necessary to protect and cushion the limb from the hard cast material, to allow a margin of room for swelling yet be applied closely enough to stabilize and maintain the reduction of the fracture. The padding also provides an interface so that when the cast saw is used to cut the cast for removal, it does not directly contact, abrade, or cut skin. Typically, a cotton or fabric stockingette is applied directly to the skin over which are wrapped multiple layers of synthetic cast padding. The cast material (plaster, fiberglass, Delta-cast) is then applied by wrapping over this padding in multiple layers to provide the hard shell as an exoskeleton to stabilize the extremity. Typically, a short arm cast (SAC) will require 2 rolls of cast padding and 2-3 rolls of 2"-3" fiberglass. A short leg cast (SLC) will use 3-4 rolls of cast padding and 3 rolls of 3" or 4" fiberglass. Pediatric casts can be difficult to apply properly and it is important that they not be too tight or too loose. Too few layers and the cast will buckle or bend, too many and it will be unnecessarily cumbersome. If the plaster or fiberglass has a pressure point or a hard edge it can result in a skin ulcer. If the entire cast is applied too tightly or the extremity subsequently swells inside the cast, the blood flow to the extremity can be compromised resulting in an ischemic limb, one of the most feared of all cast complications. As such, many surgeons and orthopedists will split a cast immediately after application to allow for some degree of swelling for several days in the immediate post-injury or post-surgical period. Proper cast application is recognized as an art. It is extremely user dependent in terms of the quality of the cast which results. This has significant ramifications in terms of fracture care outcomes, overall patient safety and cost.

A major disadvantage of the existing systems is the need for the materials (plaster, fiberglass, Delta-cast) to be immersed in water in order for an exothermic reaction to occur which will activate the hardening or curing process. Plaster or fiberglass splint or cast application requires a systematized set-up of the proper supplies and adequate preparation. This can be messy and inconvenient, and typically results in the cast padding becoming sodden with water which then must dry over time. The temperature of the water affects the length of time necessary for the cast material to cure or harden. Colder water slows the process and requires prolonged pressure or molding of the cast on the patient's extremity, while warmer water will cause the material to set more quickly, produces more heat against the skin, and if the practitioner is not adept at casting may result in hardening prematurely before the layers of cast material have been completely applied or molded. This is at once a messy, time consuming, and often times uncomfortable process for the patient. One can imagine that if one has a fracture of a long bone, such as the tibia, radius, or ulna, that any unnecessary or prolonged manipulation of the extremity will not be appreciated by the patient.

In addition, most fractures require the practitioner or physician to "reduce" (align) the broken bone so that it is in optimal anatomic position at the end of the casting application procedure before the cast fully hardens. This can be very frustrating if the resin begins to set prematurely or if anatomic alignment is difficult to maintain. If acceptable alignment is not achieved (typically confirmed by a post-casting x-ray), the cast must be cut off and the procedure repeated until an acceptable reduction is attained.

Another disadvantage of these systems is that because of sticky resins in the fiberglass, the practitioner almost always must use latex or rubber gloves to protect the hands. The patient must be draped to protect them from the sticky resin and considerable time and expense is incurred in this protection and the resulting clean up procedure. Gloves are typically used for plaster application as well due to the caustic and drying effect on skin of prolonged contact with plaster and water and the resulting mess and clean up are even more considerable.

Another disadvantage of plaster and fiberglass is the reduced visibility of the bones and soft tissues when diagnostic x-rays are obtained to follow the healing of the fractured injury over subsequent weeks. If the cast is irregular in its application, with varied thickness of the cast material, this may significantly affect visualization of the injury site. Radiology reports in which casts overlay fractures typically say, "Cast material obscures fine detail" as a disclaimer in their official dictations. Often the new bone or callus which forms at the site of a fracture is difficult to see and may be easily obscured by cast material. If a fracture is not healing properly, and a mal-union or non-union is occurring, surgery may be indicated. To remove the cast prematurely may allow the fracture to displace, to keep it on longer than necessary is not conducive to good patient care. A product which allows unimpeded x-ray visualization of a fracture would be an improvement of major significance.

Another disadvantage of plaster and fiberglass casts is that the outer layer is usually rough, hard and abrasive to other parts of the body. Sleeping can be a particularly uncomfortable experience as the hard abrasive surface quickly causes irritation as it touches other body parts, is laid on, or rubbed across the skin when rolling over.

A significant disadvantage of both plaster and fiberglass casting material is the need to use a "cast saw" for removal. These are made by a number of manufacturers but are characterized by having an oscillating curved blade which the patient is told "can't cut you." Rather it won't cut, unless the operator drags it along the skin rather than pressing down and then lifting out of the cut with an "up and down movement" to the next point of application. Unfortunately, synthetic material casts, like fiberglass, increase the chance for skin irritation, burns, and cuts. Synthetics produce heat in the cast saw blade more rapidly than plaster. Perhaps more disconcerting, they are uniformly noisy with a metallic rasp that is unnerving to most patients and especially to children. One of the more notable pediatric orthopedic texts observes: "Few things in medicine are as barbaric as a cast saw and a screaming child in the middle of the night."

Another problem with prior systems such as plaster or fiberglass is the need to completely remove the cast if it is too tight, broken, worn, the fracture needs alignment, or the cast padding gets wadded up inside the cast thus creating a pressure point. Some surgeons are adept at "wedging" casts, but in general plaster and fiberglass casts are not re-moldable or alterable once they have hardened. It is easier and safer to replace it, however time consuming or expensive. This is a common cause of emergency room visits and is a not insubstantial cost to the health care system.

SUMMARY OF THE INVENTION

The present invention solves these casting problems and others by providing a unitized multiple layer construction that uses dry-heat to soften the support layer for forming as a unitized structure to the body. These materials are pliable when heated to a temperature at which the middle support layer becomes malleable to allow conforming to a human or animal extremity and the inner layer becomes rigid when cooled to room temperature to provide support.

The cast system of a preferred embodiment may be removed by flexing open, re-heated, and re-molded as needed. This allows the cast to be easily reformed if it did not conform optimally, or if swelling increases or decreases.

The cast can be simply removed, reheated and then reformed on the patient to form a comfortable custom fit.

The applications of this system in a preferred embodiment are anticipated to significantly benefit [but are not limited to] the fields of clinical and hospital medicine (with particular importance in pediatrics, geriatrics, sports medicine, and trauma) as well veterinary medicine. This system of a particular embodiment offers an improved method of medical casting that has significant advantages in terms of:

Supplied as a unitized three layer construction is not assembled "in situ";

The forming process uses dry-heat rather than water;

Improved Radiolucency;

Does not require use of a cast saw;

Comfort reduces normal complications;

Soft comfortable inner layer eliminates padded wrappings;

Soft comfortable outer covering;

Anti-microbial inner layer

Safety—adjustability reduces risk of compressive soft tissue injury;

Ease of application—Preassembly reduces lengthy complicated application procedure;

Water proof;

Lightness;

Durability reduces need for replacement;

Improved Patient Compliance

The preferred embodiment of a casting system under the present invention is made up of several layers of materials that each provide a separate function and combine to create a unique casting product. A soft foam layer next to the skin eliminates the need for wrapped layers of roll padding typically used. It also provides insulation protection to the patient as well as insulating the middle layer to maintain the temperature of the middle layer during the casting process. A rigid plastic middle portion consisting of one or more connected parts hidden inside the foam layers, provides rigidity and support, replacing the typical plaster or fiberglass multi layer wrap.

The outer layer insulates the middle layer, hides the rigid middle layer and is comfortable for other parts of the body to touch thus preventing irritation and abrasion during activity and sleeping (which typically occurs with abrasive plaster and fiberglass systems that have no soft outer cover). The cast is completely pre-assembled before it is heated for forming and is quickly applied with one wrap around the extremity when pliable to provide a custom fit. Cooling to room temperature occurs naturally in a few minutes providing an anatomically conforming rigid cast in one step. This provides a clear advantage over the multi step, time consuming process of creating a typical "in situ" cast.

A preferred embodiment of the casting system of the present invention is made pliable and formable by dry-heat rather than the heated water of existing formable cast systems. Other typical systems use hot water to heat the material or use a moisture activated catalyst method to cure the fiberglass tape or plaster to become hardened. In this preferred embodiment, this heating can be accomplished in a specialized electric heater-pouch or a small, easily portable convection warming oven or such as are commonly found in orthopedic casting bays. The cast can also be heated in a specialized exothermic chemical reactive heating pouch such as army "meals ready to eat" are heated in the field. These thermo-moldable casts require warming to the desired temperature range until the layers are heated evenly through. The low mass and insulating features of the foam outer layers protect the skin from the heated plastic middle layer to allow people and animals to tolerate this heat without any difficulty. The product remains completely dry against the skin thus avoiding the mess and cleanup required of other wet systems as well as many hours the patient must spend wet and uncomfortable as the typical cast dries. In addition, germs and bacteria that can easily multiply in this wet environment are avoided. Antimicrobial treatment may be applied to the inner layer to further reduce the likelihood of infection.

The casting system of a preferred embodiment of the present invention enables the time necessary to precisely form the cast about the body part of the patient to be controlled. This allows the physician or technician to precisely fit the cast without rushing. This is achieved by using specific plastic mid layer materials with low forming temperatures and by the insulating factors of the foam and fabric outer layers that encapsulate the mid layer.

A preferred embodiment of the present invention provides exceptional radiolucency. The x-ray imaging quality far exceeds plaster or fiberglass. The bones of the wrist and hand are clearly visible in images using a preferred embodiment of the present invention unlike those with the fiberglass or plaster casts. The uniformity of the preferred embodiment is also much better. It is necessary to use higher milliamperes/second (mas) exposure times and/or elevated peak killivoltage (kvp) with thick fiberglass or plaster casts due to the increased density yet fracture detail often still remains poor. Reduced radiation exposure is an ongoing medical goal due to the increased risks of cancer and other associated medical illness. Although this risk is small, the 2005 report of the National Academy of Sciences BEIR VII report notes a cumulative linear no threshold (LNT) dose response to radiation exposure over a lifetime. This is of particular concern in children who may require repeated x-rays and CT scans over many years.

A preferred embodiment of the present invention does not require the use of a cast saw. It can be removed with a gentle flexing open of the product or removed with scissors. It can be trimmed with a scissors prior to, during, or following application to ensure proper fit without exposing rough edges. Avoiding the loud and noisy use of the oscillating cast saw, protects skin from injury and improves the patient care experience especially for children. The cast can also be removed intact to be re-heated and re-applied if a revised placement or fit is required.

The casting system of a preferred embodiment offers improved safety by eliminating bulky cast padding material. The inner soft foam pre-laminated layer replaces the synthetic or cotton under-wrap that often wad or bunch up beneath the splint or cast material. The product can, depending on the area of irritation, be loosened and opened to examine skin beneath. Despite admonitions to the contrary, patients often use coat hangers and the like to scratch beneath casts. Because this product is more comfortable, this tendency is reduced and should it occur, the likelihood of complications and a pressure sore is also lessened by the adjustability and absence of loose padding.

A preferred embodiment of the present invention can be loosened or tightened to a variable degree while still maintaining reduction and support. The pre-assembled cast or brace is wrapped around the extremity and overlapped to some degree (about 15% of circumference or less) with a closure system on the overlap. A hook and loop or a tensioned lace or ratchet system, allows circumferential compression of the injury to be controlled to allow for increase or decrease of swelling that often occurs with injury. It is not necessary to split or remove the cast as is common with plaster and fiberglass. It is often recommended that not only the typical cast itself but the cast padding and stockingette be cut to lessen the constrictive effects of this material which if hardened by blood or drainage can also produce limb injury or ischemia. Once split, a cast becomes less effective in maintaining the reduction of the fracture, and will need at some point to be reinforced or replaced. The preferred embodiment, because it is not wrapped and assembled "in situ" can have a closure system pre-applied to it to provide the earlier mentioned benefits.

A preferred embodiment of the present invention has the edges of the middle layer set back from the edges of the inner and outer layers. The edges of the inner and outer layer are thus laminated together at their edges. This provides soft rounded soft edges on the casting system. This increases the comfort and compliance of the patient. The hard edges of the previous casts, particularly if the cast was split would abrade and irritate the patient. These soft edges also allow the edges to overlap as discussed above. Alternatively, the edges may be wrapped in an adhesive tape to provide a soft edge.

A preferred embodiment of the present invention does not require specialized casting skills for successful application. It is significantly less user dependent than the acknowledged "art" of casting whether with plaster or fiberglass rolls. It can be applied as a single laminated sheet and conformed to the extremity. It does not require the time consuming and complicated wrapping of multiple layers of fiberglass or plaster around the limb of a patient while it is suspended by the toes or fingers. Reduction of the fracture can be accomplished in a more timely and less uncomfortable fashion. The device conforms to the limb and is applied in a single maneuver which takes little time or manipulation. The process of "reduction" (alignment) of the injury that is required for optimal healing is done immediately after the quick process of applying the cast and during the few minutes the material takes to cool and harden; this is of great import in time pressured clinics. Often, instead of delegating the oftentimes onerous and time-consuming task of casting to a dedicated cast technician or physician's assistant, the physician caregiver can apply the preferred embodiment by him/herself in the exam room in a few minutes and focus more on the reduction and alignment rather than the application of the cast. Patient satisfaction is improved. It offers a wide range of uses in the emergency room and triage situations for temporary splinting and immobilization.

A preferred embodiment of the present invention is waterproof. It has no fabric, cotton, or synthetic material between the skin and the cast to retain moisture which can be uncomfortable or cause maceration. It will not deteriorate if it becomes wet. It air dries in a brief time due to its non-absorbent properties and can be more quickly dried with a hair dryer than systems using absorbent padding layers. This has importance in terms of hygiene, recreational use, return to work, sport and veterinary utility.

A preferred embodiment of the present invention is light weight. A short arm cast (SAC) made of the preferred embodiment weighs approximately 0.35 pounds. A comparable plaster cast weights approximately 0.9 pounds and a comparable fiberglass SAC weighs approximately 0.7 pounds. This results in a greater than 50% weight savings over comparable systems. The foam layers provide featherweight padding. The rigid middle layer is a modern plastic polymer that may be perforated to as much as a 50% open pattern to improve conformity and reduce weight. The relatively light weight of the product makes it particularly attractive and more user friendly for children, the elderly, the infirm, and for veterinary applications. With development, its use in making pediatric hip spica casts, scoliotic casts, and thoraco-lumbar-sacral (TLSO) orthoses offers significant advantages in terms of comfort and tolerability for these unfortunate individuals. With clearance by sporting and work organizations, it offers the ability for injured athletes and workers to return to competition and the workplace, depending on circumstances, more rapidly. This too has significant economic ramifications.

A preferred embodiment of the present invention is durable. It uses modern synthetic thermoplastic technology and the science of tubular and cylindrical physics to provide stabilization and support without sacrificing lightness. The mechanical properties of the rigid middle plastic layer (and also the foam layers) can be varied by using different materials, thicknesses or perforations to provide precisely the desired rigidity, flexibility and even hinging as desired for each medical application. These lexing/rigidity features can be achieved without sacrificing durability by using polymer materials that allow the desired degree of flexing, yet resist fatigue and cracking over a long cycle life. When compared with typical plaster or fiberglass systems, which are not so easily engineered, and have poor resistance to flexing and fatigue, the benefits of the preferred embodiment are of great value.

Veterinary uses of casting systems provide another challenge in that animals tend to chew on casts and braces. Using a very resilient rigid middle layer and a durable outer foam layer (perhaps with taste deterrents) that is engineered to resist dental stress can provide great benefit over rigid fiberglass casting materials that quickly crack and splinter when chewed.

A preferred embodiment of the present invention, in the final analysis, markedly improves compliance in the use of the product and by doing so improves the final outcome. Patients will wear a more comfortable less intrusive cast longer to achieve the final measure of healing. This product, for the reasons cited above, offers an improved method of moldable casting that promises to revolutionize the way we currently treat fractures and other skeletal injuries.

These and other features of the present invention will be evident from the detailed description of preferred embodiments and from the drawings.

DETAILED DESCRIPTION OF THE DRAWINGS

A preferred embodiment of the present invention is illustrated in FIGS. 1-29. It is to be expressly understood that the descriptive embodiments are provided herein for explanatory purposes only and are not meant to unduly limit the claimed inventions. The exemplary embodiments describe the present invention in terms of cast systems used for immobilizing and supporting body part as shown in FIGS. 1-29. It is to be understood that the present invention is intended for use with other types of medical, sports, veterinary and other types of uses.

Overview

Figure 1:
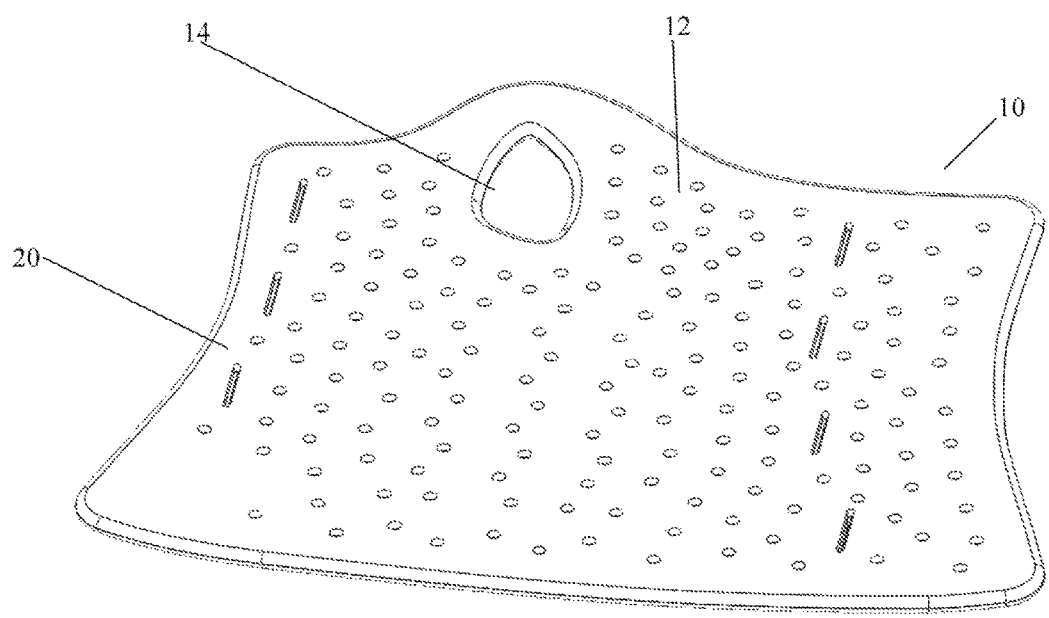
FIG. 1 is top view of a unitized casting system of a preferred embodiment of the present invention.
Figure 2:
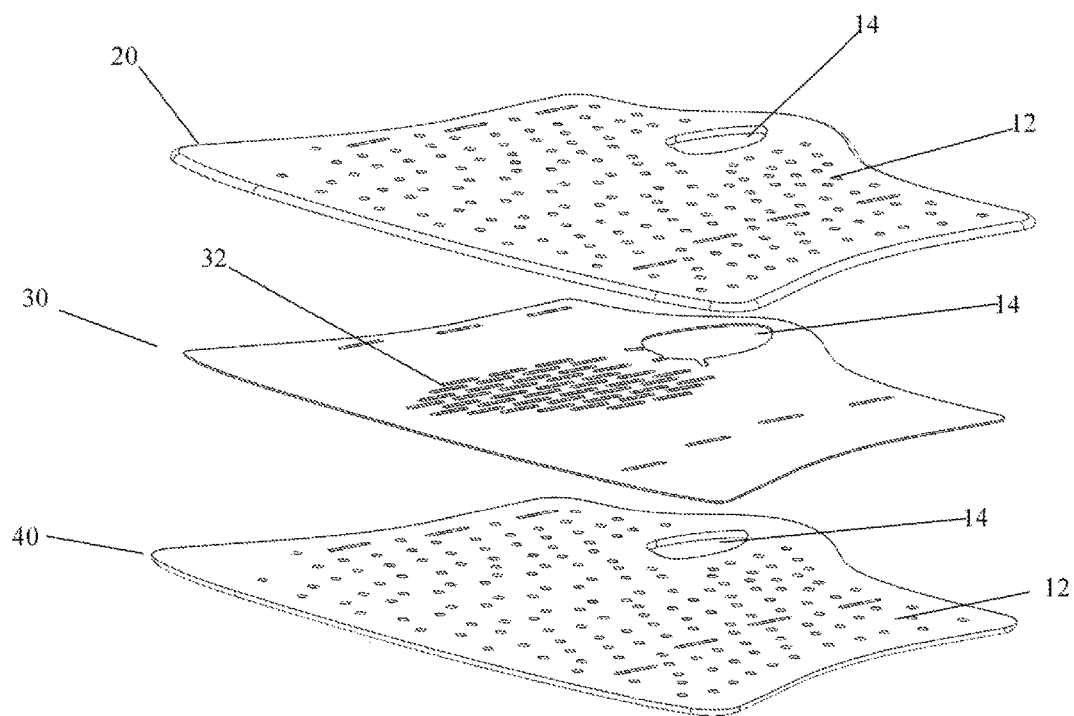
FIG. 2 is a disassembled view of the layers of the embodiment of FIG. 1.
Figure 3:
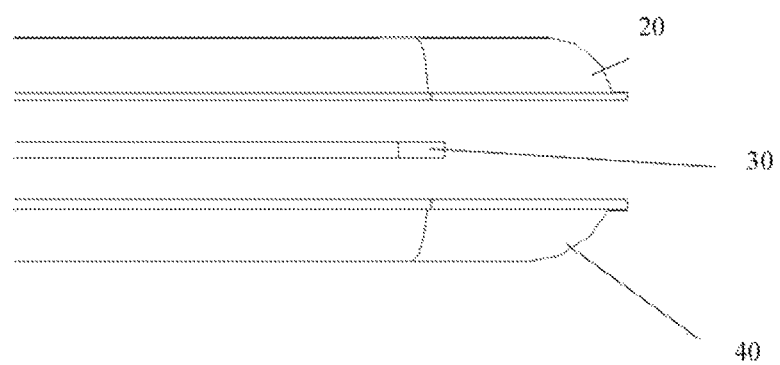
FIG. 3 is a detail view of the disassembled view of the layers of the embodiment of FIG. 1.
Figure 4:
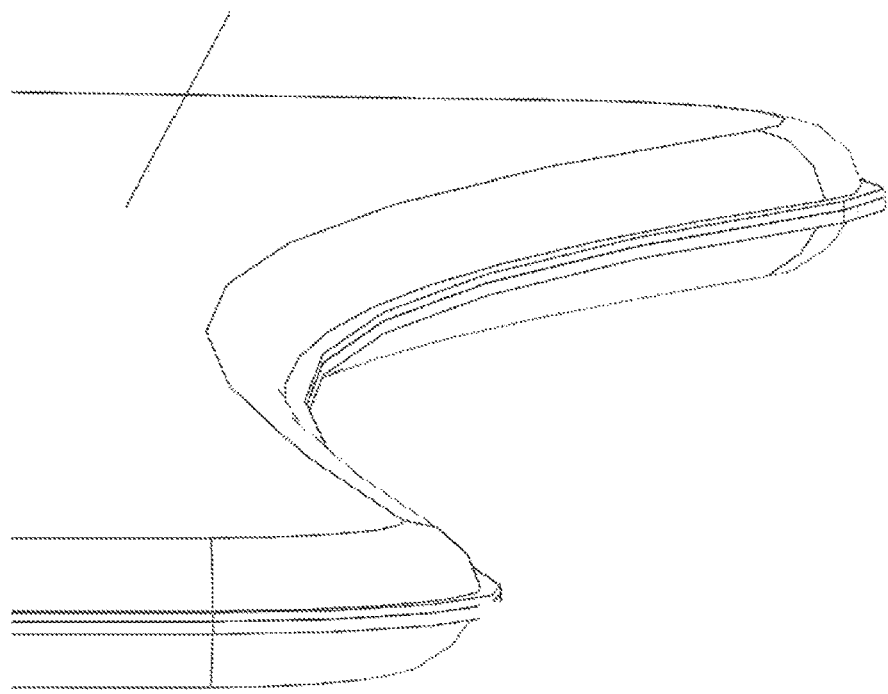
FIG. 4 is a detailed view of the assembled embodiment of the embodiment of FIG. 1.
Figure 5:
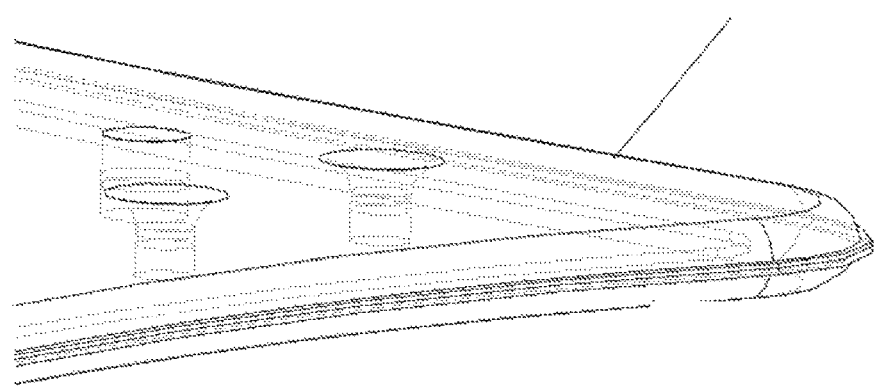
FIG. 5 is another view of the assembled embodiment of the embodiment of FIG. 1.

The system, in a preferred embodiment, provides a unitized casting system that is far superior to previous systems. The system of a preferred embodiment of the present invention, as used as a cast, is shown in FIGS. 1-6. This cast system is illustrated as a wrist cast but it is to be expressly understood that it can be used for any type of casting situation, such as but not limited to foot casts, neck casts, leg casts, arm casts etc. This cast system 10 of this embodiment includes an outer durable padding layer 20, a mid support layer 30 and an inner comfort padding layer 40 as shown in FIG. 2. The three layers each provide unique functions and when combined into a unitized cast create a unique and superior cast. The three layers, each described in greater detail below, are molded or laminated together to form a unitized cast. Closures 50 are applied prior to use that enable a health care provider without specialized training to easily form the cast in an appropriate shape and secure the cast to the patient. The resulting cast is much more comfortable for the patient and can increase the patient's compliance with its use. The resulting cast has many additional benefits over the previous systems as discussed above and below.

The unitized system of this preferred embodiment enables the cast to be pre-laminated, pre-shaped or in blank sheets and provided in sizes according to a desired use, such as for supporting a wrist, arm, knee, neck or other body location. The system is then easily customized to the particular patient as discussed below. The system, in a preferred embodiment, also allows the cast to adjust as necessary by the patient to accommodate swelling or other issues. This adjustability also allows the cast to be customized to the particular body part being supported.

The casting system is heated with dry heat to become thermoformable for shaping within a few minutes. The casting system at temperatures between 160 degrees Fahrenheit to 250 degrees Fahrenheit (the Target Temperature) is pliable for ease in shaping but still is able to maintain some degree of stiffness so not to be overly fluid that is reach beyond the glass transition temperature of the material. The system can then be placed on the patient without burning or causing discomfort to the patient during this process. The relatively low density foam inner layer insulates the high density hot middle plastic layer from the body. The skin, having a higher density than the foam, actually cools the foam more rapidly than the foam can transfer heat to the skin thus protecting it from burning at the temperatures used. The system is then formed to the exact shape desired for that particular patient easily and without the need of specialized skill using a method described below.

The system of a preferred embodiment is designed to allow the time during which the casting system is malleable to be controlled. This is referred to herein as the "dwell time" for the cast. This is a critical time in that it is the time that physician or technician has to precisely mold the cast onto the patient's body. This preferred embodiment controls the dwell time by the selection of the middle layer material, the density/thickness of the middle layer material, the temperature range at which the middle material is malleable and the insulative qualities of the inner and outer layers. In addition, dwell time can be adjusted by the user depending on the temperature the item is heated to, higher temperatures resulting in longer dwell times.

The unitized casting system of this preferred embodiment includes a soft inner foam layer 40 assembled by laminating or molding or other manufacturing processes to the mid support layer 30. The inner foam layer 40 provides comfort next to the skin. It can protect the patient's skin from abrasion and heat from the mid layer 30 as well as being water proof (non absorbent). This layer may be formable at the Target Temperatures to provide a precise fit to the smallest details of the patient. The particular foam composition for this layer is low density as discussed above to dissipate heat so the patient is not harmed when the warm cast is initially placed around the body part. In other preferred embodiments, the foam may not be malleable but is able to compress to comfortably fit closely around the body part of the patient. The foam provides cushioning as well to increase the comfort and compliance of use. The foam in the preferred embodiment is of a closed cell construction though alternatives may be open cell to provide breath-ability if waterproof features are not desired. This layer may also be of a foam formulation to accept and dispense therapeutic chemical additives such as antimicrobials, skin lotions or other medicines and chemicals. In addition, visco-elastic memory foam may be used for this layer to conform precisely to the body.

This inner layer 40 in the preferred embodiment is formed from a foam material, such as from a variety of cross-linked Polyethylene ("PE") and Ethylene Vinyl Acetate ("EVA") foams or other suitable materials. The material of the inner layer is moldable at the Target Temperatures. However, this layer may also be moldable at higher temperatures about 300 degrees Fahrenheit which are achieved in the manufacturing process. This allows the material to be compression molded into various forms during manufacturing and for the edges to be heat sealed closed to the outer layer thus encapsulating the mid layer. This layer can be treated with various medicines or antimicrobial treatments.

An additional layer may also be molded inside of the inner layer to provide anti-microbial features. Other therapeutic properties may be incorporated as well into these additional layers. This layer could be foam, fabric, non-woven fabric or other suitable material.

The middle layer 30 of this preferred embodiment is a thin thermoformable polymer plastic material that becomes pliable at the Target Temperature yet substantially rigid at room temperature. This layer provides a substantial amount of support for the body part. It may be engineered to have varying degrees of flexibility and rigidity as desired by varying the polymer material composition. The features may also be varied by the material thickness or by perforations or cut-outs. This layer may be molded with varied thicknesses, tapered edges, ribbing, holes and features that provide the desired rigidity, strength and flexibility required for the intended healing purpose.

The middle layer 30 of the preferred embodiment is preferably formed from Polyvinyl Chloride ("PVC") sheet, Amorphous Polyethylene Terephthalate ("APET"), Recycled Polyethylene Terephalate ("RPET") or PVC foam such as Sintra™, or Komatex™.

Other preferred materials include without limitation polycaprolactone, and caprilactone. Also such materials as Low or High Density Polyethylene ("HDPE") and similar materials may be used as well. Additional materials that are thermoformable at temperatures below 250 degrees Fahrenheit while rigid at room temperatures may be used as well.

One key feature to making this layer easily conformable to the three dimensional surfaces of the body is to perforate it with small holes 32 close together resulting in an open structure from 25% to 50% open. This method creates a matrix framework around the holes that, when heated and pliable, can more easily form by deforming around the small holes 32, moving into the small holes 32 or stretching the small holes 32 apart. With this perforation method, thicker stiffer materials can be used than would not normally be adequately formable without the perforations. Perforating also allows the plastic polymer to be formed at lower temperatures than a continuous layer due to deforming process mentioned above which is important for patient comfort and safety. The thick matrix framework when cool and formed in a cylindrical fashion becomes very rigid as needed for the most supportive casts. In addition, weight is reduced by the perforations which increase the comfort and compliance of the patient. These perforations to the middle layer are separate from the ventilation holes that are used for ventilation and cooling purposes which must be punched through all of the layers and are intended to be larger and further apart. In a preferred embodiment of the present invention, the perforations remove between twenty-five to sixty percent of the weight of the middle layer. These perforations are particularly useful when the material for the middle layer includes PVC sheet, APET and RPET.

Alternatively, foam materials, such as PVC foam (including Sintra™ and Komatex™) and APET may be foamed when extruded or molded with 20 to 50 percent air or gas bubbles instead of perforations. Other foamed materials may be used such as rigid EVA foams and other high density foamed polymers. Their use depends on the desired rigidity and durability required for each use.

The middle layer 30 may have a varying topography such as by having increased thicknesses in areas where additional rigidity is desired and decreased thicknesses in areas where more flexibility is needed.

The middle layer 30 may also include multiple layers of heat formable material. These different materials may include different characteristics of rigidity and heat formability, or they may only be on certain areas of the middle layer to increase rigidity or flexibility at certain areas of the middle layer. Also, additional materials may be inserted in the middle layer at desired locations to provide additional rigidity or flexibility as needed.

The outer layer 20 is another foam layer that, in a preferred embodiment, has many of the features of the inner layer including providing insulation against the heat of the middle layer when forming the cast about a body part. Additionally it provides aesthetics to the cast and also provides protection from abrasion from the middle layer. It is intended to provide a durable and comfortable covering to the rigid and perhaps rough perforated middle layer. In a preferred embodiment, the outer layer is formed from a foam, such as urethane foam, foam rubber or EVA foam that is moldable at a temperature above the Target Temperatures. This allows the outer layer to be thermoformed during manufacturing with relief features, ribs, depressions or cosmetic shapes and to have the edges sealed to the inner layer at temperatures considerably higher than the Target Temperatures. Such features would not be affected during the patient forming process. The outer layer, in the preferred embodiment, does not thermoform at the Target Temperature, but will stretch to follow the shape of the mid layer. Since it does not thermoform, it will not pick up the imprint of the elastic wrap or compression tube and will remain smooth and attractive in appearance. It can be thermoformable at the Target Temperature if these features are not desired.

The outer foam layer may also be of a stiff foam to provide additional support, as well as environmental protection, aesthetics and also to provide some support during the thermoforming process. When comparing this outer layer with the typical abrasive plaster or fiberglass cast outer surface, significant improvements in comfort, appearance, aesthetics, durability and ease of use can be experienced. Also, fabric, synthetic leather or other cosmetic covering may be laminated to the outside of this layer for purposes of aesthetics or durability. In addition, fabric can be applied known as unbroken loop which has a surface compatible with common hook and loop fasteners such as Velcro™. This allows closures, extra supports, multi-part casts and other devices to be instantly connected using common hook strip fasteners.

The cast may perforated through the three layers to form ventilation holes 12 in various amounts and shapes to provide ventilation, forming features, access to wounds or access to catheters etc. These apertures also allow the middle layer to expand and shrink as necessary as the cast is being molded to the body part. The unitized cast may also be perforated to create apertures 14 for body parts such as thumbs, toes, etc. It may also be perforated to accept various closure system attachments. In most cases, the preferred embodiment is wrapped once around the extremity and overlapped to some degree. This is to accommodate the varied body diameters and shapes encountered within each sized product and is a feature not found with typical plaster and fiberglass casts. The overlap is also the spot where the closure devices will be placed that allow the cast to be opened or closed in circumference during use.

The middle layer 30 is sandwiched between the inner layers 40 and outer layer 20 and recessed from the edges of those layers during the molding process. In this process, the layers are all heated above the Target Temperature for manufacturing. The mold includes a cut-off line on its outer edge to cut the foam of the inner layer 40 and outer layer 20 as well as any fabric layers. In addition, next to the cut-off line a bar compresses the layers to a high degree. The edges of those layers are pinched to seal the edges of the cast 10 tightly closed permanently bonding all layers in the molding process. This provides a clean, soft, rounded thin edge to the cast that is durable, comfortable and less prone to abrade the skin which is a common problem with traditional plaster and fiberglass casts.

Alternatively, the edges may be sealed with an edge tape on the exposed edges. This allows the cast to be formed in blank sheets and custom cut for a particular purpose. The edge tape seals the exposed edges and also forms a soft edge. This tape can be of a flexible thin fabric or foam with an adhesive backing that is easily applied by hand to edges of the cast where desired.

The assembly process of the preferred embodiment uses molding, laminating or any other manufacturing process to form the multiple layers in a single unitized cast. One such process is compression molding which typically includes the following steps:

Laminating of fabrics and coverings to the foam layers.

Die-cutting blanks of each layer.

The plastic sheet mid layer will be die cut and may have fasteners and other features attached. It gets put inside the layers and is set back from the edges.

Heating the foam and fabric layers to the critical molding temperature, above the Target Temperature range where they will be permanently formable.

Placing them into a compression mold that also cuts features (vent and closure attachment holes) and the perimeter while sealing the edges with a compression bar.

The cold metal, wood or plastic mold is compressed and forms the relief patterns in all of the layers as well as punches holes and seals the edge perimeter.

The foam cools by the mold and holds its shape.

All of this must be done at a molding temperature and adhesive temperature so that when the product is reheated to the Target Temperature, it remains intact and the relief patterns do not balloon back out to flat.

An alternative is to use a hot mold that forms the layers by heating them under high compression which are then cooled after forming.

Figure 6:
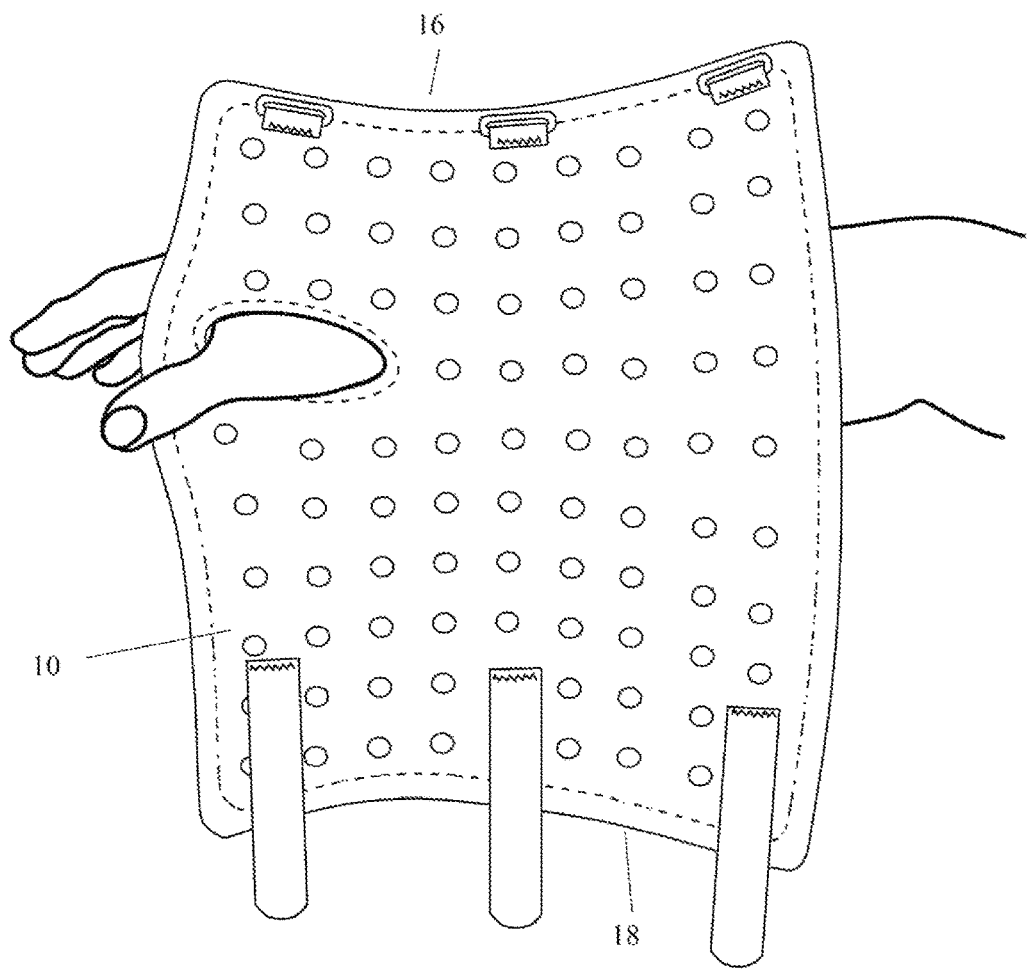
FIG. 6 is a side view of the embodiment of FIG. 1 being mounted onto a wrist.
Figure 7:
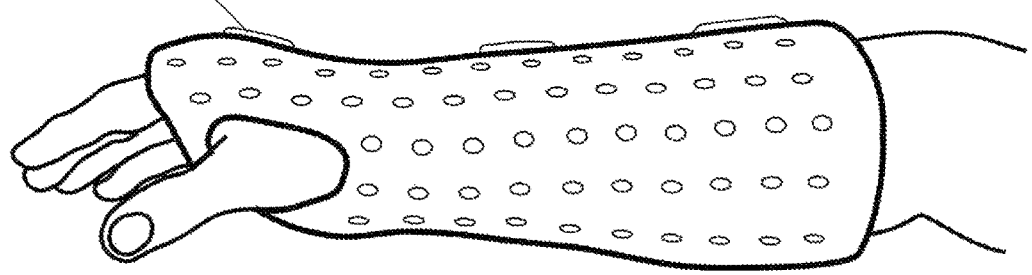
FIG. 7 is a side view of the unitized cast of the embodiment of Figure mounted onto a wrist after compression forming.
Figure 8:
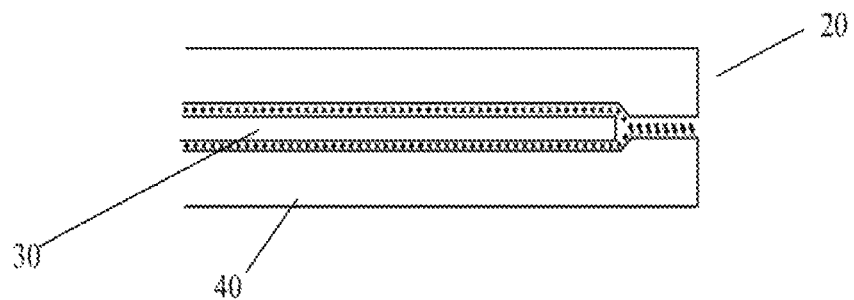
FIG. 8 is a cross sectional view of the unitized cast that is laminated.
Figure 9:
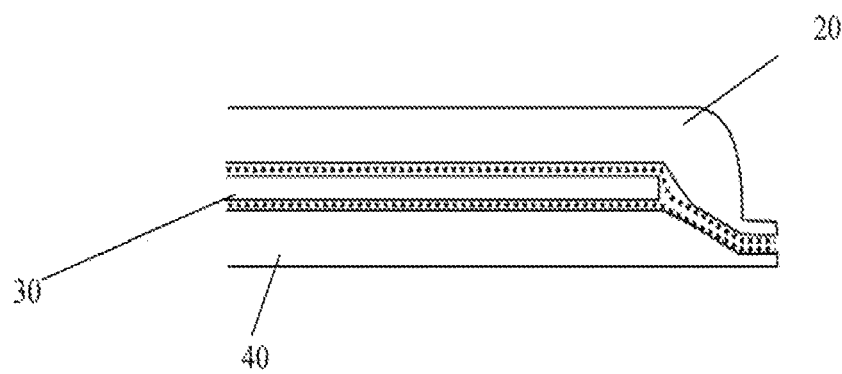
FIG. 9 is a cross sectional view of the unitized cast that is laminated with the edges molded.
Figure 10:
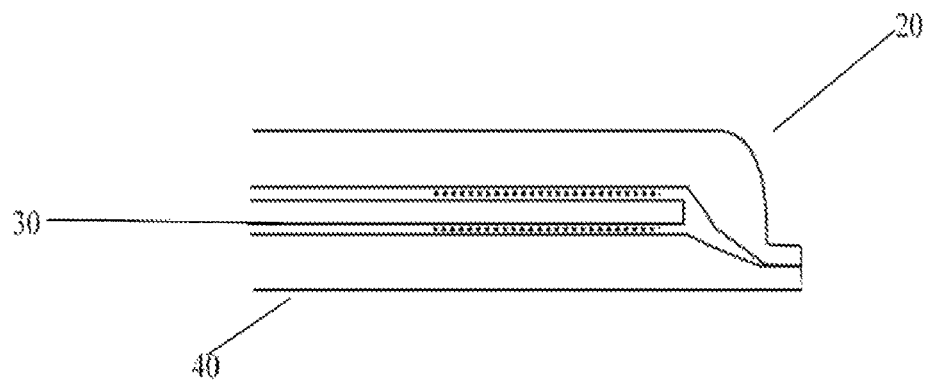
FIG. 10 is a cross sectional view of the unitized cast that is molded with heat and spot adhesive.

This embodiment does not require lamination as the parts are molded together. However, this embodiment may also include the layers 20, 30 and 40 laminated together as shown in FIGS. 6 and 7. The outer layers extend beyond the middle layer to form a soft edge. The edges of the outer layers may be laminated as shown in FIG. 8, laminated and molded as shown in FIG. 9 or molded with heat sealed edges and spot adhesive as shown in FIG. 10.

A critical feature provided by a preferred embodiment of the present invention is the ability to control the dwell time of the middle layer. The dwell time is the time that the middle layer is formable, before it begins to cool beyond its malleability temperature. This is the time that the physician or casting technician has to properly form the cast onto the body part. In this preferred embodiment, the dwell time is controlled by the initial temperature that the middle layer is heated, by the material choice for the middle layer, by the thickness and perforations or foaming (density) of the middle layer, and by the insulative characteristics of the inner and outer layer. This preferred embodiment uses materials for the rigid middle layer that become malleable at temperatures at or below 250 degrees Fahrenheit. The forming temperature range of these materials by themselves would not normally enable the material to be malleable for a sufficient time and would cause severe discomfort or injury to the patient. These materials by themselves would cool in a matter of seconds when removed from the heat source. The encapsulation in the low density insulating foam inner and outer layers is an important innovation that increases the dwell time and allows it to be varied by the above means while at the same time, insulating the patient for the dangerous heat of the inner layer. The ratio of the perforations in the middle layer is also selected so that the middle layer has sufficient density to retain the heat and to maintain rigidity while being more easily formed due to the perforations.

Figure 11:
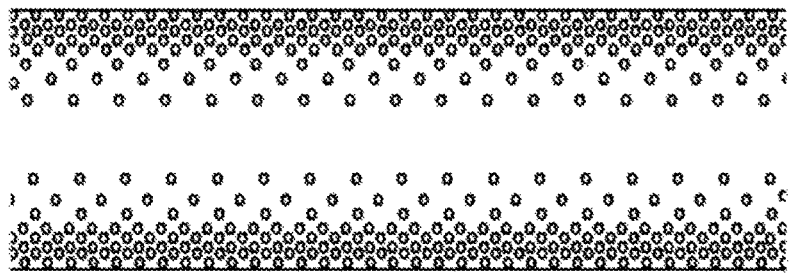
FIG. 11 is another preferred embodiment using a single material layer having a higher density inner portion and a lower density on the outer surfaces.
Figure 12:
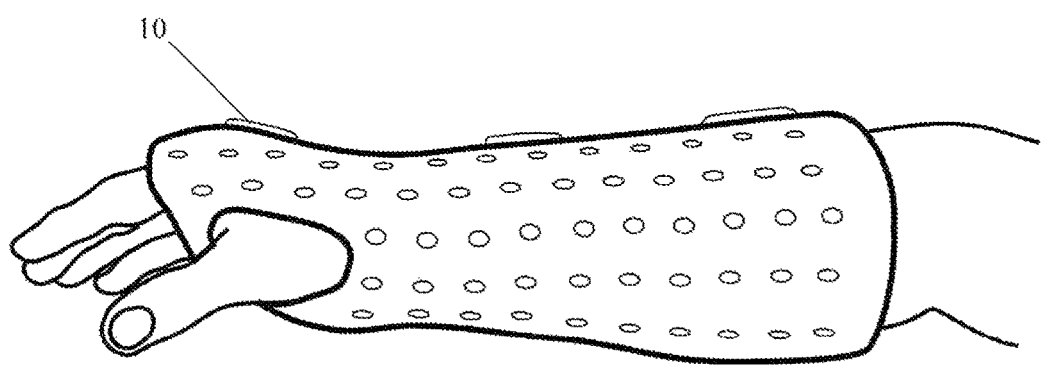
FIG. 12 is a view of a side view of the cast applied to the wrist of a patient.

In another preferred embodiment of the present invention, the entire cast system is formed from a single material and behaves in much the same manner as described for the multi layer cast above. This material as shown in FIG. 11 would have strata that are more and less dense by incorporating more or less gas bubbles into a foam material. The center portion of the material has a higher density (less or no gas bubbles) than the outer portions of the material (more gas bubbles). This can be accomplished by using a foam extruded material where the foam is crushed or manipulated during the manufacturing process so it becomes more dense. It is then processed with heat or other means so the surface lofts and the gas bubbles expand and becomes less dense and more cushioned. This could also be achieved by co-extruding or co-molding multiple layers at the same time which could be foamed to different densities or using different compositions of materials co-extruded. The net effect is a single material sheet with a stiff center portion and cushioning, insulating outer portions. The lower density (more foamed) outer portions of the material can then insulate the inner portion during the forming process about the body part protecting it from discomfort from the heat of the inner portion. This insulation also provides sufficient dwell time for the cast to be formed about the body part extending the time the center portion is pliable. Additional layers can be added as well to provide additional therapeutic and aesthetic benefits.

A fastening system 50 is used to secure the cast closed about the body part as shown in FIGS. 12-15 and to allow some degree of compression to hold the injury in reduction. This system may be double sided adhesive tape placed in between the overlap, adhesive tape applied to the seam or circumferentially, or a mechanical closure system. These mechanical closures may consist of, but are not limited to, hook and loop fastener, snaps, laces, toothed zip ties, ratchet lace systems, ski boot type buckles and the like. In a preferred embodiment, the closure system can be fastened and the tension adjusted by the attending doctor or technician as the cast is applied with a tamper proof closure so it cannot be adjusted by the patient. It can be later re-adjusted by the attending doctor or technician by means of a tool to access the tamper proof adjustable closure. If desired by the attending doctor or technician, the closure could be set so the patient has the means to only loosen or tighten the cast a limited amount but it cannot be prematurely removed. This allows the patient to loosen the cast if there is discomfort or swelling and tighten it if too loose without going back to the physician. In addition, the system could be set by the attending doctor or technician so the patient has the ability to adjust and completely remove the cast. This can extend the life of the cast so it can be used as a temporary brace to protect the partially healed injury during rigorous use. Using this controllable and adjustable system, the attending doctor or technician has options appropriate for all phases of healing and can enable or lock out the patients' ability to make adjustments.

Figure 13:
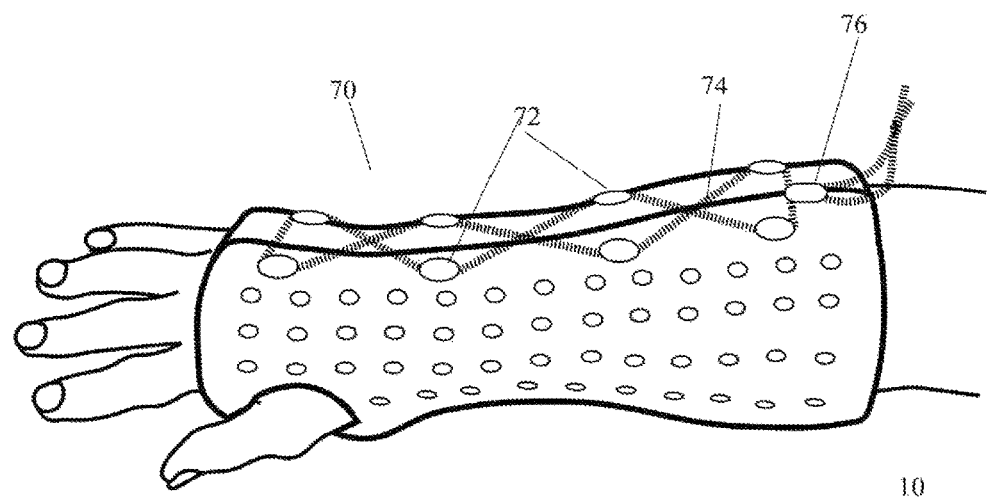
FIG. 13 is view of another alternative securing mechanism of the cast system of FIG. 1.
Figure 14:
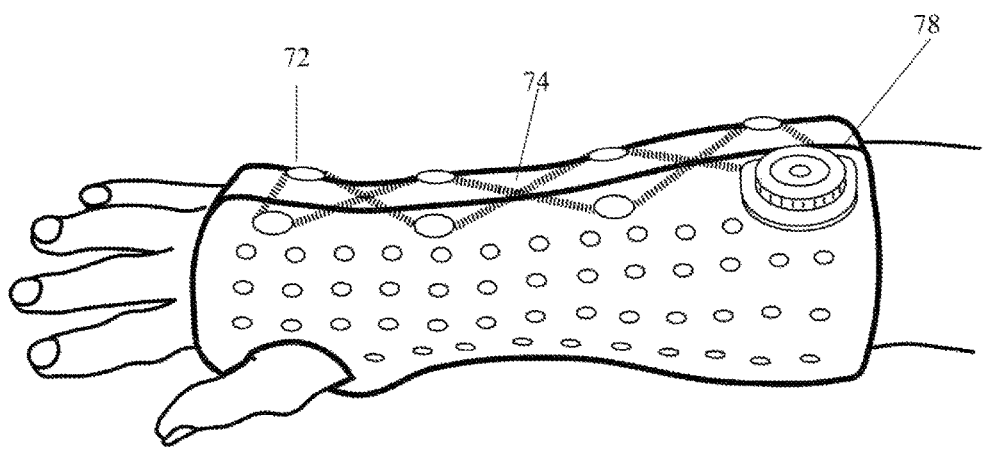
FIG. 14 is view of another alternative securing mechanism of the cast system of FIG. 1.
Figure 15:
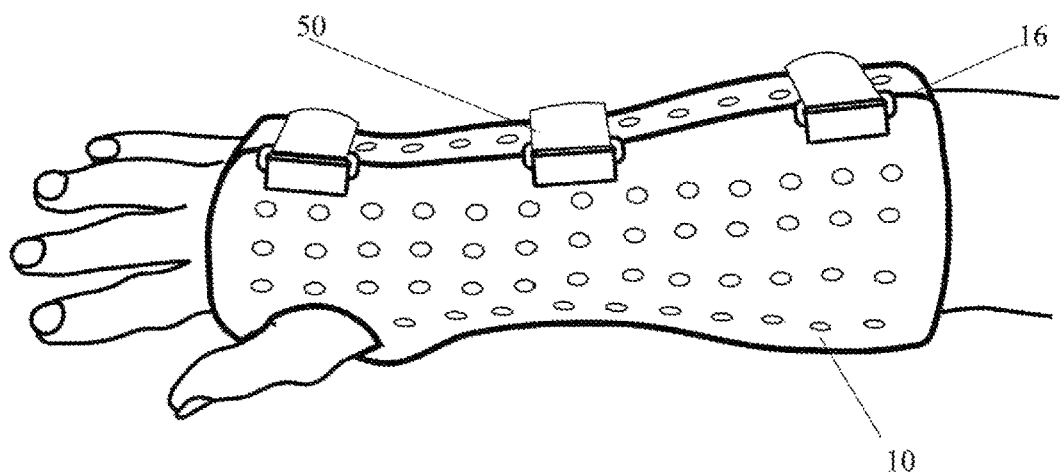
FIG. 15 is a view of a securing mechanism of the cast system.

One attachment mechanism in particular includes a tensioning cable system 70 as shown in FIG. 13. The system 70 utilizes a series of guide members 72 on opposite sides of the cast system 10. Lace 74 is laced through guide members 72 on alternate sides as shown in FIG. 13 and then through locking member 76. The lace is drawn tight so the cast has the appropriate tension on the body part and locked into place. An alternative lacing system shown in FIG. 14 is similar to the above mechanism but utilizes a reel mechanism 78 to mechanically tighten and lock the tightened lace that can be easily released and tightened with micro adjustments. These systems can have features mentioned in the above paragraph regarding the attending doctor or technician's ability to lock out patient access to adjustment or allow varied degrees of adjustability built into the mechanism. Another type of securing system includes the use of straps as shown in FIG. 15.

Figure 16:
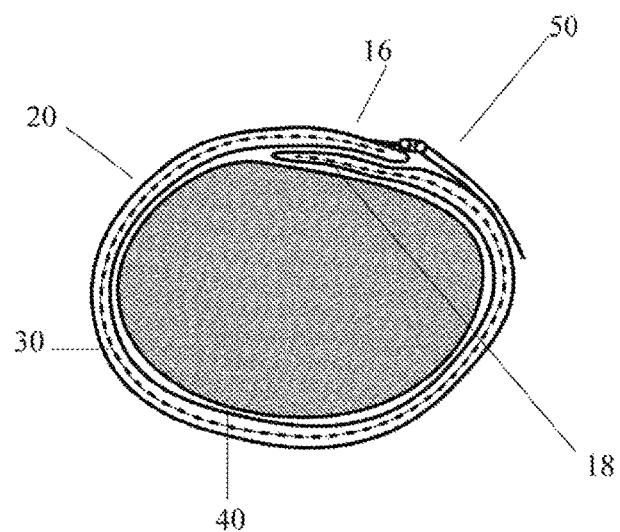
FIG. 16 is a cross-section view of the cast system of the embodiment of FIG. 15.

The securing mechanism 50 of the casting system 10 of a preferred embodiment allows the edges of the casting system to overlap. This overlap amounts to about twenty-five percent (25%) of the circumference or less. The closure system discussed above is mounted on this overlap. This increases the adjustability of the casting system to increase or decrease the compressibility on the injured body part. The unitized casting system 10 may be provided in various sizes to fit different body parts and sizes of body parts. The adjustable overlap 80, as shown in FIG. 16 of the unitized casting system of this preferred embodiment provides further capability to custom fit the cast to a particular body part of a particular patient. The securing mechanism 50 allows the cast to be adjusted by increasing or decreasing the amount of the overlap to more closely fit the patient's body part.

The cast, when warm, soft and pliable must be formed to the intimate shapes of the body to best stabilize the injury under reduction. A loose fitting cast with voids between the body and cast can allow undesired movement. A perfectly formed cast that meets every detail of the body can provide stabilization without being excessively tight and in many cases, just meeting the body without compressive force. This is the most comfortable configuration that will provide the needed support yet not constrict, reduce circulation or irritate. In order to achieve this desired effect, a unique method of forming this cast to the body must be incorporated. Since the overlap opening 80 as shown in FIG. 9 that is formed from side edges 16, 18 of the cast is adjustable in circumference, this cast is best formed when warm and pliable by applying compressive circumferential force in excess of the comfortable level for long term wear. Once the cast is cool and rigid in a few moments, this compression can be removed and the closures can be adjusted to provide the desired amount of closure of the cast for comfort and stabilization.

Figure 17:
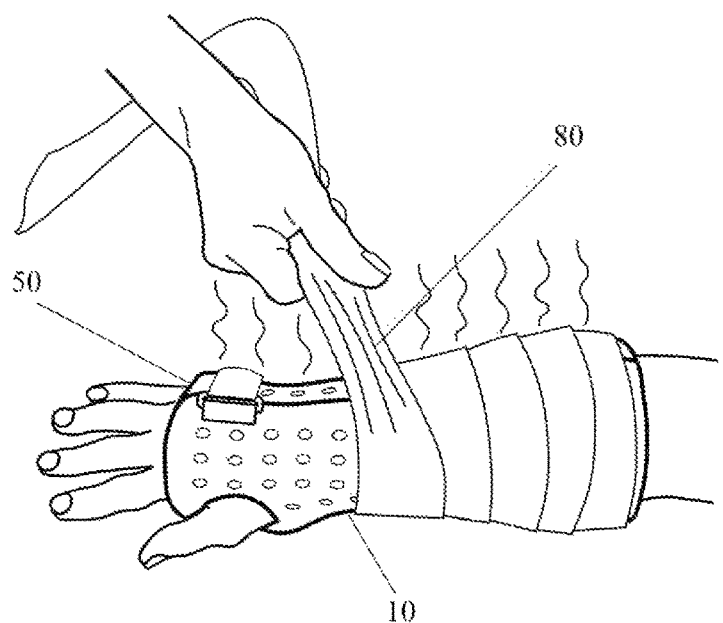
FIG. 17 is a perspective view of the cast system undergoing compression for shaping about the patients' wrist.

The preferred method of compression identifies two options. An elastic band as shown in FIG. 17 can be quickly wrapped around the warm pliable cast as soon as it is installed. This elastic band may be fabric or rubberized material in the appropriate width, thickness and elasticity for the particular cast type in a length to adequately wrap over the entire cast. Compressive pressure can be varied simply by pulling on the band as it is wrapped. This process will insure that every part of the cast is formed to the body and voids are not created. It should be expressly understood that, though this process is commonly used to apply compressive pressure to wounds, it is a unique process to apply it to temporarily form a cast that is in a warm and pliable state for the duration of cooling, then to be removed.

Figure 18:
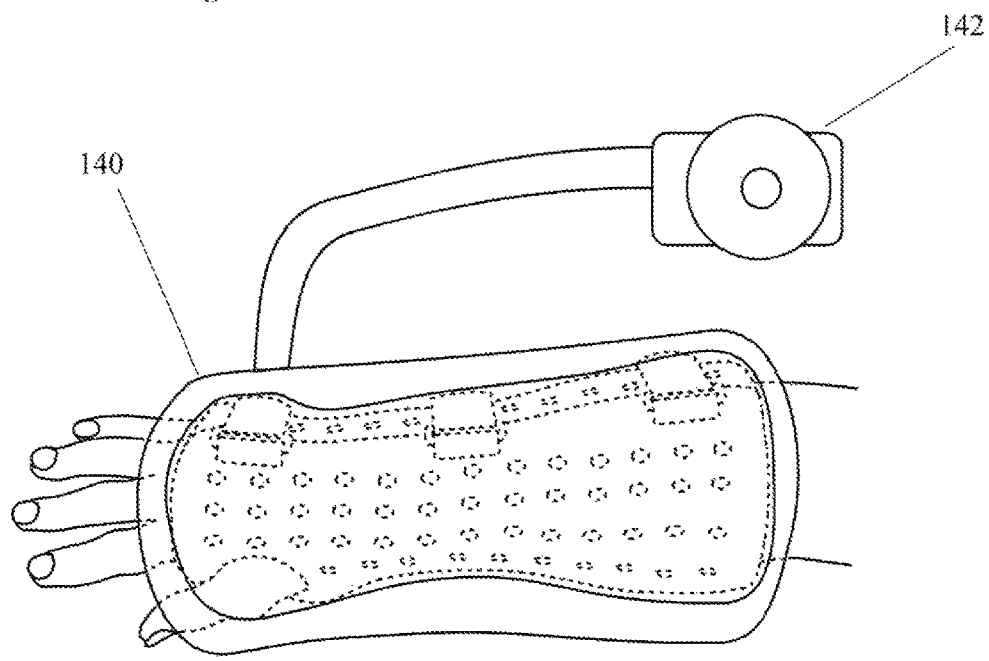
FIG. 18 is a perspective view of the cast system undergoing compression for shaping with a compression tube.

Another method of forming with compressive pressure is that of an inflatable double walled cuff as shown in FIG. 18. The cuff would be appropriately sized to the extremity or adjustable in circumference and slid on the body part and cast while it is still warm and pliable. Air pressure is pumped into the cuff to apply compressive force as desired to form the cast and it is removed when cooled.

The above unique combination of cast features provides a lightweight yet structurally rigid cast that is easily custom formed to the patient on site without the need for specialized training or skills. The resulting cast is patient compliant and can be adjusted as needed to increase compliance with its use. The adjustability can also decrease soft tissue injuries. The cast can be formed with dry heat so many heat sources can be used. The patient is protected from damage or discomfort from the heated cast during the forming process. The cast is waterproof and durable and can be reused and reshaped as needed. The materials used, being mostly polymers, provide a high degree of radiolucency. The body part can be examined through x-rays without the need to remove the brace as compared with Fiberglass and plaster which are not typically radiolucent. There is a reasonable potential for using recycled polymers in the construction of the middle layer that may impact the beverage container industry.

The unitized casting system of this preferred embodiment may be provided in a relatively flat shape or generally in the shape for a specific body part, such as a wrist, ankle, knee or other body part as well as in general sizes, such as large, medium, small. The casts may also be pre-formed in some cases to approximately fit the body part for trial of size or in the case where a more complex structure requires it. The system can then be heated and custom shaped to specifically fit the body part that it is to support. The adjustable overlap also contributes to this custom fitting as discussed above. The unitized casting system will then fit the body part in a comfortable yet rigid manner.

Figure 19:
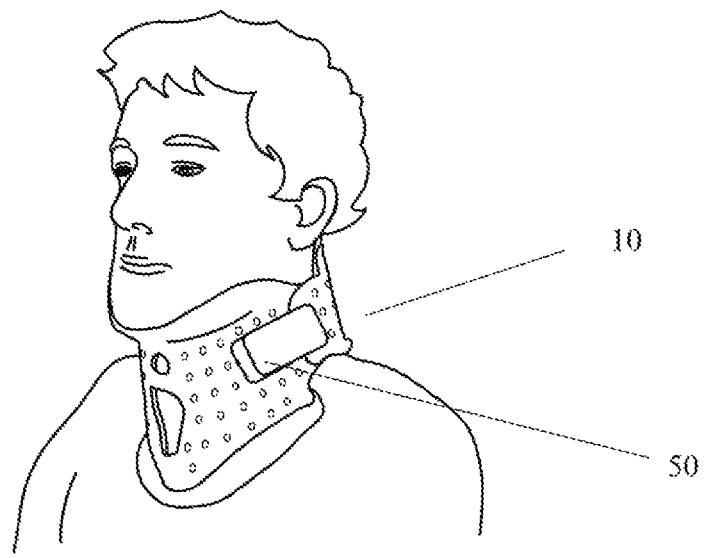
FIG. 19 is a perspective view of a neck cast using the preferred embodiment of the invention.
Figure 20:
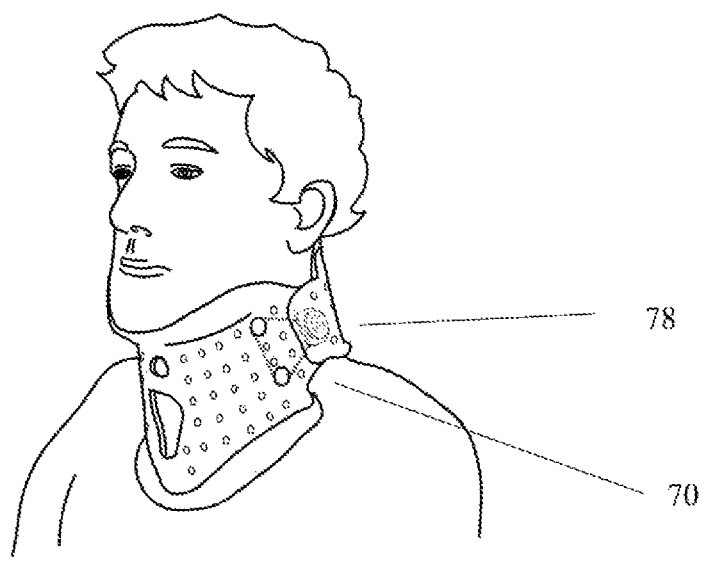
FIG. 20 is a perspective view of the neck cast of FIG. 19 with an alternative securing mechanism.
Figure 21:
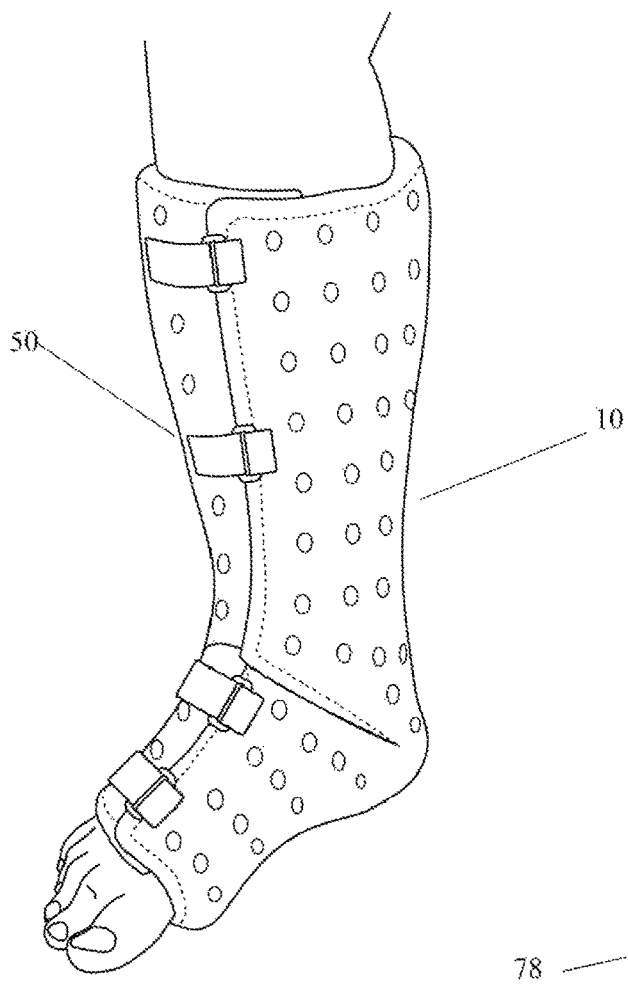
FIG. 21 is a perspective view of a foot cast using the preferred embodiment of the invention.
Figure 22:
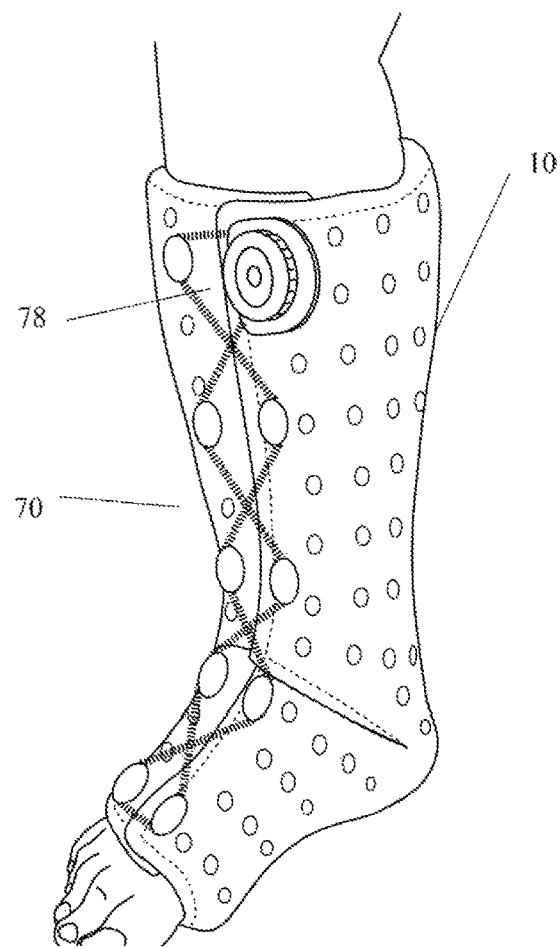
FIG. 22 is a perspective view of the foot cast of FIG. 21 with an alternative securing mechanism.

Examples of the preferred embodiments of the present invention used in other types of casts are shown in FIGS. 19-22. An example of a neck cast is shown in FIGS. 19 and 20. This use is of particular advantage since this area of the body is particularly sensitive and the contour shape varies greatly from person to person. A custom moldable, adjustable tension devise for this use that is soft foam lined and covered with an attractive outer layer can greatly increase the comfort and healing of the patient. A foot cast is shown in FIGS. 21 and 22. This use has advantages brought by the durable nature of the materials used since they are less prone to fatigue and cracking under body weight. In addition, the ability to adjust tension in this area prone to swelling is of great advantage. The unitized casting system 10 can be thermoformed utilizing a dry heat source in lieu of typical water activated materials presently in use. One disadvantage of these typical materials is that the body part, and often wounds associated with the injury are wetted during the casting process. They typically remain wet many hours after casting causing the skin to become uncomfortable, abraded and more prone to build up of microorganisms at precisely the time when sterility is most desired. Examples of the preferred embodiments of the present invention stay dry during the casting process and provide only a brief and comfortable dry heating of the body part. Healing begins in a dry environment less prone to the buildup of microorganisms and infection. The use of antimicrobial treatments incorporated inside the cast can be more effective in this dry environment.

The casting system can also be shaped and secured to the body part without the need for extensive training since it is pre-made and not built on the patient. These pre-made casts have most of the labor done at the factory where they are manufactured saving valuable high cost hospital and clinic time adding considerable advantage. The casting system is also waterproof, lightweight and comfortable thus enhancing the patient's compliance in the use of the system. The polymer plastics used are much more durable than fiberglass or plaster and resist fatigue and cracking. This combined with ability to adjust the tension and size of the cast or remold it can allow a single cast to be used throughout the healing process where typical casts are replaced 1-3 times upon repeated visits to the hospital or clinic.

Application

In use, the unitized casting system 10 is provided as a kit to the individual, the orthopedic specialist, physician, technician, first responder or other entity. The appropriate kit type and size for the body part to be supported is selected. A dry heat source is applied to the cast 10 until the cast is sufficiently pliable to allow it to be shaped. This should be in the range 160 F to 300 F (Target Temperatures). The dry heat source can be an oven, microwave, or as discussed below, a heat bag, an internal heating mechanism or an exothermic heat source.

Figure 23:
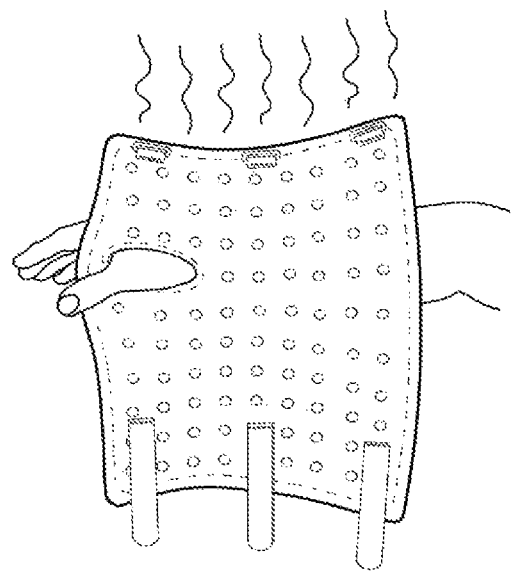
FIG. 23 is a side view of the heated cast being placed about a patient's wrist.
Figure 24:
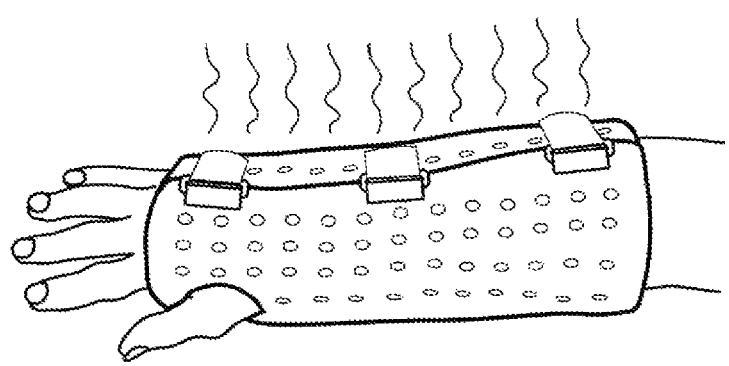
FIG. 24 is a view of the heated cast secured on the patient's wrist before compression molding.
Figure 25:
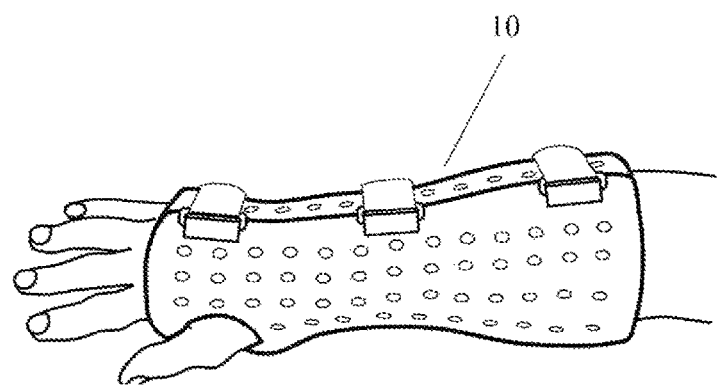
FIG. 25 is a perspective view of the cast system cooled and secured about the patient's wrist.

Once the cast is sufficiently heated and pliable, approximately 5-10 minutes, it is applied directly to the body part as shown in FIGS. 23-25. The lower density polymer foam that makes up the inner layer 40 dissipates the heat so that that the individual does not suffer any pain or discomfort from the heat. The cast will be pliable, in the preferred embodiment, for about three to ten minutes. This allows ample time to form the cast about the body part. FIG. 15 shows the cast loosely fitted before compression molding to the body. An elastic wrap 80 is utilized to provide compression to mold entire cast specifically to the body part as shown in FIG. 17. The elastic wrap 80 applies pressure uniformly over the cast 10. The elastic wrap 80 can be an elastic band, or an elastic compression bandage formed from nylon/tricot knit, rubber, urethane, spandex or any other suitable material. Alternatively, as shown in FIG. 18, a compression tube 140, that is a double walled pneumatic tube, is slipped over the warm cast 10. The tube is inflated by hand pump 142 to apply pressure uniformly over the warm cast until the shape of the cast conforms to the body part. Comparing FIG. 23 with FIG. 25 shows how the compression molding method shapes the cast to the intimate contours of the body.

The combination of the pliable heated thermoformable layers along with the uniform pressure forms the cast to the body part. The mid layer provides the majority of the shape and support. The inner layer, if formed of a thermoformable material will also shape to conform about the body part as well. The outer layer, in the preferred embodiment, does not thermoform, but will stretch to follow the shape of the mid layer. Since it does not thermoform, it will not pick up the imprint of the elastic wrap or compression tube and will remain smooth and attractive in appearance. This layer can be thermoformable at the Target Temperature if these features are not desired.

Once the shape of the cast has been achieved, the elastic wrap 80 is removed or the compression tube 140 is deflated and removed. The cast is secured to the body part by securing closure 50. The cast will support the body part as well as remain comfortable during its use. The cast can easily be removed if necessary and reformed as needed.

Heat Sources

Figure 26:
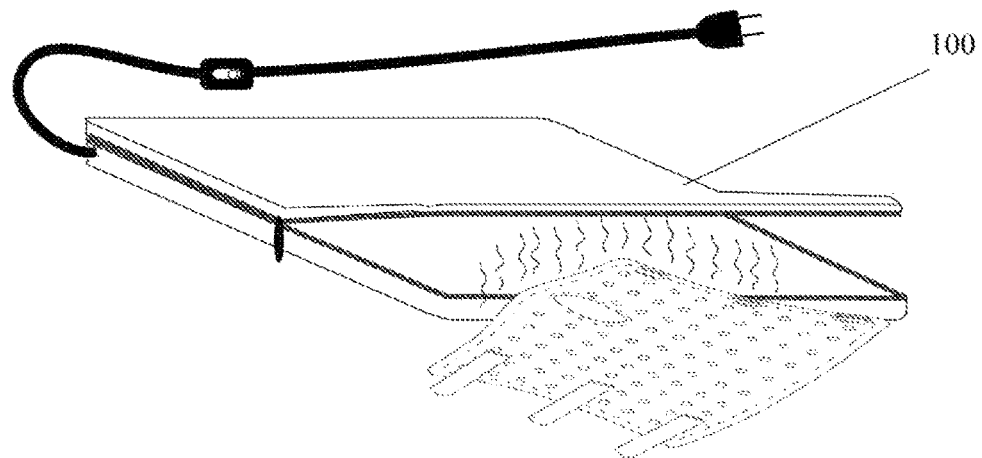
FIG. 26 is a perspective view of the dry heat pouch of a preferred embodiment of the present invention.
Figure 27:
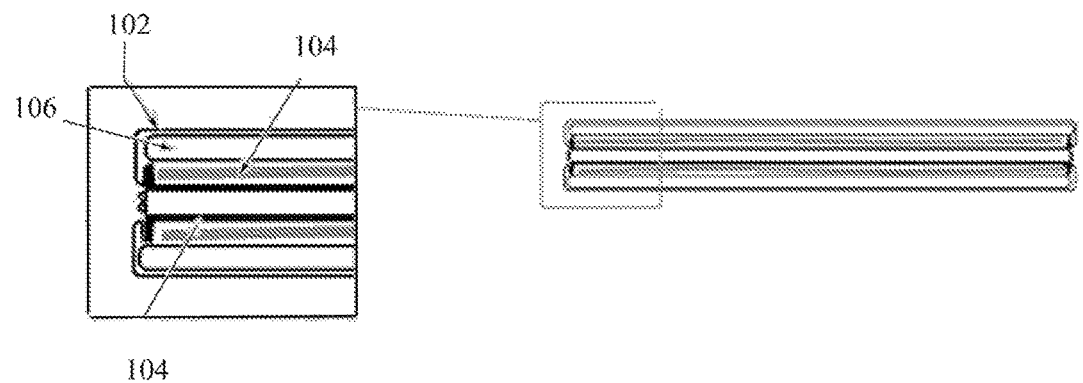
FIG. 27 is a cross-section view of the dry heat pouch of the embodiment of FIG. 18.

The present invention also, in a preferred embodiment, provides a heat source for heating the casts to the Target Temperature as described above in order to shape the system to the body part. One preferred embodiment of the heat source, as shown in FIG. 26, includes a heating pouch 100 that is easily stored and transported. The heating pouch includes an outer insulation layer 102, opposing heating elements 104 in a sheet fashion and a liner bag 106, as shown in FIG. 27, preferably durable on the outside and non-stick on the inside, that holds the heating element and insulation. The heater elements can be made of electrical heat wire or heating foil or other electrically activated design. The heater bag 100 is easily opened to accept the cast and closes during the heating process. A closure system such as hook and loop, zipper of buckles closes the bag to hold in heat. The heater element is connected to an electrical power source, either 110-240 V AC standard plug for connection to an electrical outlet, or a 12 V transformer or a 12V DC battery or vehicle electrical power source and maintains the Target Temperature accurately via a thermostat or heat control device. The heating pouch may also include an optional temperature probe that monitors the temperature applied to the bracing system.

In use, the unitized casting system 10 is placed in the case between the opposing heater elements. The case is activated causing the heater elements to heat the cast 10. Once the cast is heated sufficiently to the Target Temperature and adequately pliable, it is removed for application and forming around the body part.

This heat source case is easily transported and able to be used in hospitals, clinics, training rooms or even on site for treating an injury. Special ovens or chemical reactions are not needed.

Another heat source of a preferred embodiment of the present invention uses an internal heating mechanism built into the unitized cast. This may be an electric grid on one or both sides of the middle layer. This grid is connected to a power supply which supplies electric current to heat the middle layer to the target temperature. Once forming of the cast is complete, the electric current is turned off and the cast quickly cools. This eliminates the need for an external heating device since it is built into the cast.

Figure 28:
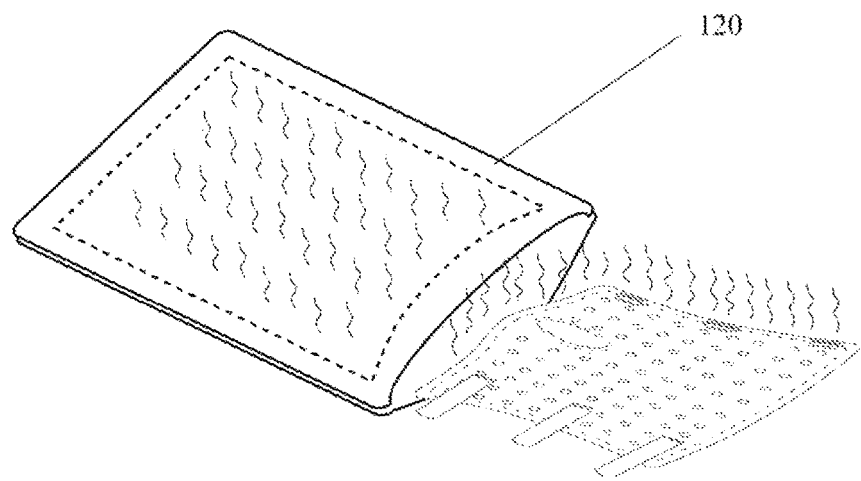
FIG. 28 is a perspective view of an exothermic heat pouch of a preferred embodiment of the present invention.

Another heat source under a preferred embodiment of the present invention utilizes an exothermic heat source 120 as shown in FIG. 28. A number of chemical reactions exist that produce heat such as carbon/air, Lye/water, air batteries and others. When two or more elements are exposed to each other, the resulting chemical reaction causes heat to be released. Typical common uses are carbon/air packets used as pocket heaters for cold weather and Lye/water containers used to heat army "Meals ready to eat". Similar systems can be used to heat the casts of the preferred embodiment to the Target Temperature by incorporating the heating chemicals into a plastic pouch or bag with adequate room to insert the cast. The chemical reaction is made and the cast heated, removed and applied. The advantage of such a system is that injury often occurs in the field where medics or doctors do not have access to electricity. This method provides a quick simple method to heat the cast in a self contained fashion and apply it in the methods described above.

Figure 29:
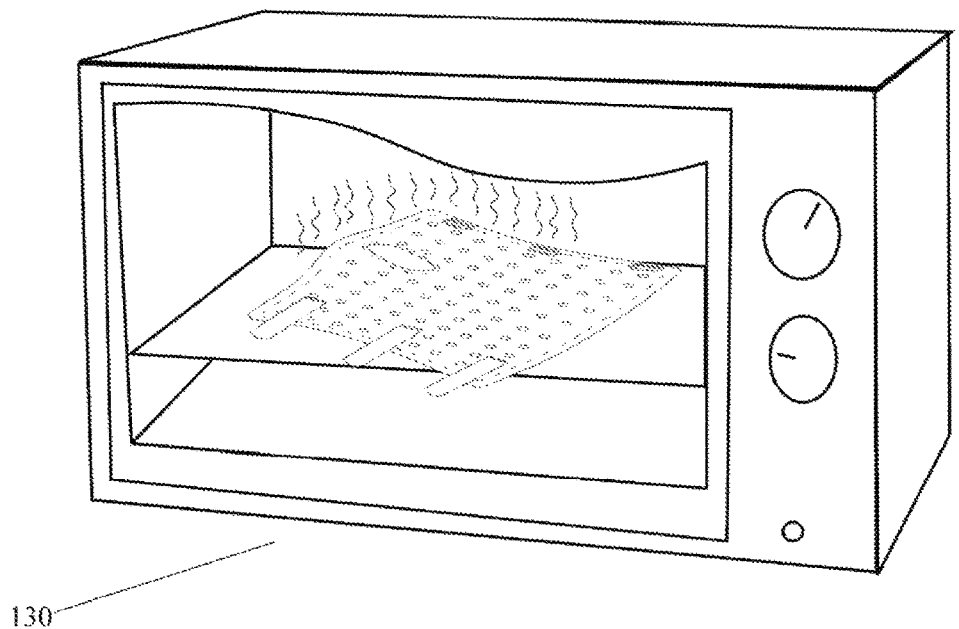
FIG. 29 is a perspective view of a dry heat oven of a preferred embodiment of the present invention.

Other heating means include convection ovens, toaster ovens, radiant lamp heat sources, Infrared heaters and microwave ovens. A convection forced air oven 130 may be used as well as shown in FIG. 29. Microwave heating does not typically heat polymers, however, special additives or layers could be used to trap the heat provided by microwaves. Another method for heating in a microwave is to place the cast inside of a plastic bag containing a small amount of water or liquid. The liquid is quickly heated by the microwave and thus heats the cast. Other embodiments may be used as well that provide a dry heat source for heating the cast system to temperatures up to about 250 degrees Fahrenheit. These systems may also include timers as well as temperature probes and alarms when the temperature of the cast system has reached the desired temperature.

These and other features of the present invention are considered to be within the scope of the invention as claimed. The above descriptions are provided for exemplary purposes and are not intended to limit the scope of the claimed invention.

The invention claimed is:

1. A cast system for supporting a body part, said cast system comprising:
   a composite support shell comprising:
      a middle polymer layer moldable within and above a target temperature range and generally rigid below the target temperature range;
      a flexible inner foam layer configured to conform to the middle layer and moldable either within and above the target temperature range or above a molding temperature, the molding temperature being above the target temperature range; and
      a flexible outer foam layer configured to stretch to conform to the middle layer and moldable above the molding temperature,
   wherein the composite support shell comprises a relief pattern extending through the inner foam layer, middle polymer layer, and outer foam layer formed in the composite support shell when heated above the molding temperature, the relief pattern configured to at least partially conform the support shell to the body part, and
   wherein the composite support shell is configured to maintain the relief pattern at temperatures below the molding temperature.

2. The cast system of claim 1, wherein the composite support shell is a generally flat sheet.

3. The cast system of claim 2, wherein the relief pattern comprises a curved portion in the generally flat sheet.

4. The cast system of claim 3, wherein the composite support shell comprises an aperture positioned in the curved portion.

5. The cast system of claim 4, wherein the aperture is configured to receive a thumb.

6. The cast system of claim 1, wherein the inner foam layer is moldable within and above the target temperature range.

7. A cast system for supporting a body part, said cast system comprising
   a polymeric foam support shell moldable within a target temperature range for conforming to the body part and comprising air cells dispersed throughout, the polymeric foam support shell further comprising:
      a middle stratum for providing rigid support to the body part, the middle stratum having a first density of air cells;
      an inner stratum for providing insulation and cushioning, the inner stratum having a second density of air cells; and
      an outer stratum for providing insulation, the outer stratum having a third density of air cells,
   wherein the second density and third density are each higher than the first density such that the middle stratum is more rigid than the inner stratum and the outer stratum and such that air encapsulated in the air cells of the inner stratum and the outer stratum insulates the middle stratum so that the middle stratum remains within the target temperature range for a longer period of time than the outer stratum and the inner stratum when the polymeric foam support shell is heated to a temperature within or above the target temperature range.

8. The cast system of claim 7, wherein the middle stratum has no air cells.

9. The cast system of claim 7, wherein the second density is approximately the same as the third density.

10. The cast system of claim 7, wherein the air cells are closed cells.

11. The cast system of claim 7, wherein the air cells are open cells.

12. The cast system of claim 7, wherein the polymeric foam support shell is formed of a material selected from the group consisting of: amorphous polyethylene terephthalate, recycled polyethylene terephthalate, polyvinyl chloride, polyvinyl chloride foam, polycaprolactone, caprilactone, polyethylene, and derivatives of those materials.

13. The cast system of claim 7, further comprising an additional layer of material coupled to an inner surface or an outer surface of the polymeric foam support shell.

14. A cast system for supporting a body part, said cast system comprising
   a composite support shell having an inner surface and an outer surface comprising:
      a middle layer moldable within a target temperature range so that the composite shell may be conformed to the body part and generally rigid below the target temperature range to support the body part;
      a flexible inner layer configured to conform to the middle layer; and
      a flexible outer layer configured to stretch to conform to the middle layer,
   a plurality of ventilation holes spaced generally uniformly across the composite support shell and extending from the inner surface to the outer surface, the ventilation holes each having an open cross-section passing through the inner layer, the middle layer, and the outer layer,
   wherein the ventilation holes are configured to allow the middle layer to expand into the open cross-section of the ventilation hole when the middle layer is molded to the body part and to provide ventilation to the body part.

15. The cast system of claim 14, wherein one or more of the ventilation holes provides a forming feature for conforming the composite support shell to the body part.

16. The cast system of claim 15, wherein the forming feature is an area of higher flexibility.

17. The cast system of claim 14, wherein one or more of the ventilation holes is sized and configured to provide access to a wound.

18. The cast system of claim 14, wherein one or more of the ventilation holes is sized and configured to allow a catheter to access the body part through the composite support shell.

19. The cast system of claim 14, wherein the plurality of ventilation holes comprises ventilation holes of different shapes.

20. The cast system of claim 14, wherein the plurality of ventilation holes comprises ventilation holes of different sizes.

* * * * *